(12) United States Patent
Li et al.

(10) Patent No.: US 10,314,699 B2
(45) Date of Patent: Jun. 11, 2019

(54) RECAPTURABLE VALVE-GRAFT COMBINATION AND RELATED METHODS

(71) Applicant: St. Jude Medical, Cardiology Division, Inc., St. Paul, MN (US)

(72) Inventors: Xue Mei Li, Shoreview, MN (US); Brian Joseph Perszyk, Shoreview, MN (US); Mike Meyer, Minnetrista, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 66 days.

(21) Appl. No.: 15/041,321

(22) Filed: Feb. 11, 2016

(65) Prior Publication Data
US 2016/0262880 A1 Sep. 15, 2016

Related U.S. Application Data

(60) Provisional application No. 62/132,609, filed on Mar. 13, 2015.

(51) Int. Cl.
*A61F 2/24* (2006.01)
*A61F 2/07* (2013.01)
(Continued)

(52) U.S. Cl.
CPC .............. *A61F 2/2418* (2013.01); *A61F 2/07* (2013.01); *A61F 2/24* (2013.01); *A61F 2/06* (2013.01); *A61F 2/2409* (2013.01); *A61F 2/2436* (2013.01); *A61F 2/848* (2013.01); *A61F 2/856* (2013.01); *A61F 2/89* (2013.01);
*A61F 2002/061* (2013.01); *A61F 2002/065* (2013.01); *A61F 2002/072* (2013.01);
(Continued)

(58) Field of Classification Search
CPC .......... A61F 2/07–2002/077; A61F 2/24–2475
See application file for complete search history.

(56) References Cited

U.S. PATENT DOCUMENTS

| | | | |
|---|---|---|---|
| 3,657,744 A | 4/1972 | Ersek | |
| 4,275,469 A | 6/1981 | Gabbay | |

(Continued)

FOREIGN PATENT DOCUMENTS

| | | |
|---|---|---|
| DE | 198 57 887 A1 | 7/2000 |
| DE | 101 21 210 A1 | 11/2002 |

(Continued)

OTHER PUBLICATIONS

Ruiz, Carlos, Overview of PRE-CC Mark Transcatheter Aortic Valve Technologies, Euro PCR.
(Continued)

*Primary Examiner* — Yashita Sharma
*Assistant Examiner* — Rebecca S Preston
(74) *Attorney, Agent, or Firm* — Lerner, David, Littenberg, Krumholz & Mentlik, LLP

(57) ABSTRACT

A therapeutic device includes a prosthetic heart valve including a collapsible and expandable stent having an aortic section and an annulus section, and a valve assembly disposed within the annulus section of the stent, the valve assembly including a plurality of leaflets; and a graft coupled to the aortic section of the stent. The graft has a body and at least one lining disposed on the body and defining a lumen therethrough.

21 Claims, 17 Drawing Sheets

(51) Int. Cl.
  *A61F 2/848* (2013.01)
  *A61F 2/89* (2013.01)
  *A61F 2/856* (2013.01)
  *A61F 2/06* (2013.01)

(52) U.S. Cl.
  CPC . *A61F 2002/075* (2013.01); *A61F 2210/0014* (2013.01); *A61F 2210/0057* (2013.01); *A61F 2210/0076* (2013.01); *A61F 2220/0016* (2013.01); *A61F 2220/0058* (2013.01); *A61F 2220/0075* (2013.01); *A61F 2220/0083* (2013.01); *A61F 2250/007* (2013.01); *A61F 2250/0015* (2013.01); *A61F 2250/0039* (2013.01)

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| 8,840,663 B2 | 9/2014 | Salahieh et al. |
| 8,931,159 B2 | 1/2015 | Hillukka |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0210304 A1 | 10/2004 | Seguin et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0112309 A1 | 4/2009 | Jaramillo et al. |
| 2009/0125098 A1* | 5/2009 | Chuter ............... A61F 2/07 623/1.26 |
| 2009/0138079 A1 | 5/2009 | Tuval et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |

(56) References Cited

U.S. PATENT DOCUMENTS

| | | |
|---|---|---|
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2012/0303116 A1 | 11/2012 | Gorman, III et al. |
| 2015/0025625 A1* | 1/2015 | Rylski ............... A61F 2/2412 623/2.14 |
| 2015/0142100 A1* | 5/2015 | Morriss ............... A61F 2/2418 623/2.4 |
| 2016/0143732 A1* | 5/2016 | Glimsdale ............ A61F 2/2418 623/2.41 |

FOREIGN PATENT DOCUMENTS

| | | |
|---|---|---|
| DE | 102005003632 A1 | 8/2006 |
| DE | 20 2008 009 610 U1 | 12/2008 |
| EP | 0850607 A1 | 7/1998 |
| EP | 1 000 590 A1 | 5/2000 |
| EP | 1 360 942 A1 | 11/2003 |
| EP | 1 584 306 A1 | 10/2005 |
| EP | 1 598 031 A2 | 11/2005 |
| EP | 1926455 A2 | 6/2008 |
| FR | 2 847 800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 0149213 A2 | 7/2001 |
| WO | 01054625 A1 | 8/2001 |
| WO | 01056500 A1 | 8/2001 |
| WO | 01076510 A2 | 10/2001 |
| WO | 0236048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 07071436 A2 | 6/2007 |
| WO | 08070797 A2 | 6/2008 |
| WO | 10008548 A2 | 1/2010 |
| WO | 10008549 A1 | 1/2010 |
| WO | 10096176 A1 | 8/2010 |
| WO | 10098857 A1 | 9/2010 |

OTHER PUBLICATIONS

Percutaneous aortic valve replacement: resection before implantation, 836-840, Quaden, Rene et al., European J. of Cardio-thoracic Surgery, 27 (2005).

Catheter-implanted prosthetic heart valves, Knudsen, L.L., et al., The International Journal of Artificial Organs, vol. 16, No. 5 1993, pp. 253-262.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

Is It Reasonable to Treat All Calcified Stenotic Aortic Valves With a Valved Stent?,579-584, Zegdi, Rachid, MD, PhD et al., J. of the American College of Cardiology, vol. 51, No. 5, Feb. 5, 2008.

"Direct-Access Valve Replacement", Christoph H. Huber, et al., Journal of the American College of Cardiology, vol. 46, No. 2, (Jul. 19, 2005).

"Percutaneous Aortic Valve Implantation Retrograde From the Femoral Artery", John G. Webb et al., Circulation, 2006; 113:842-850 (Jun. 2, 2006).

"Minimally invasive cardiac surgery", M. J. Mack, Surgical Endoscopy, 2006, 20:S488-S492, DOI: 10.1007/s00464-006-0110-8 (presented Apr. 24, 2006).

"Transapical Transcatheter Aortic Valve Implantation in Humans", Samuel V. Lichtenstein et al., Circulation. 2006; 114: 591-596 (Jul. 31, 2006).

"Closed heart surgery: Back to the future", Samuel V. Lichtenstein, The Journal of Thoracic and Cardiovascular Surgery, vol. 131, No. 5, pp. 941-943.

"Transapical approach for sutureless stent-fixed aortic valve implantation: experimental results"; Th. Walther et al., European Journal of Cardio-thoracic Surgery 29 (2006) 703-708 (Jan. 30, 2006).

"Transapical aortic valve implantation: an animal feasibility study"; Todd M. Dewey et al., The annals of thoracic surgery 2006; 82: 110-6 (Feb. 13, 2006).

Textbook "Transcatheter Valve Repair", 2006, pp. 165-186.

Design U.S. Appl. No. 29/375,243, filed Sep. 20, 2010.

\* cited by examiner

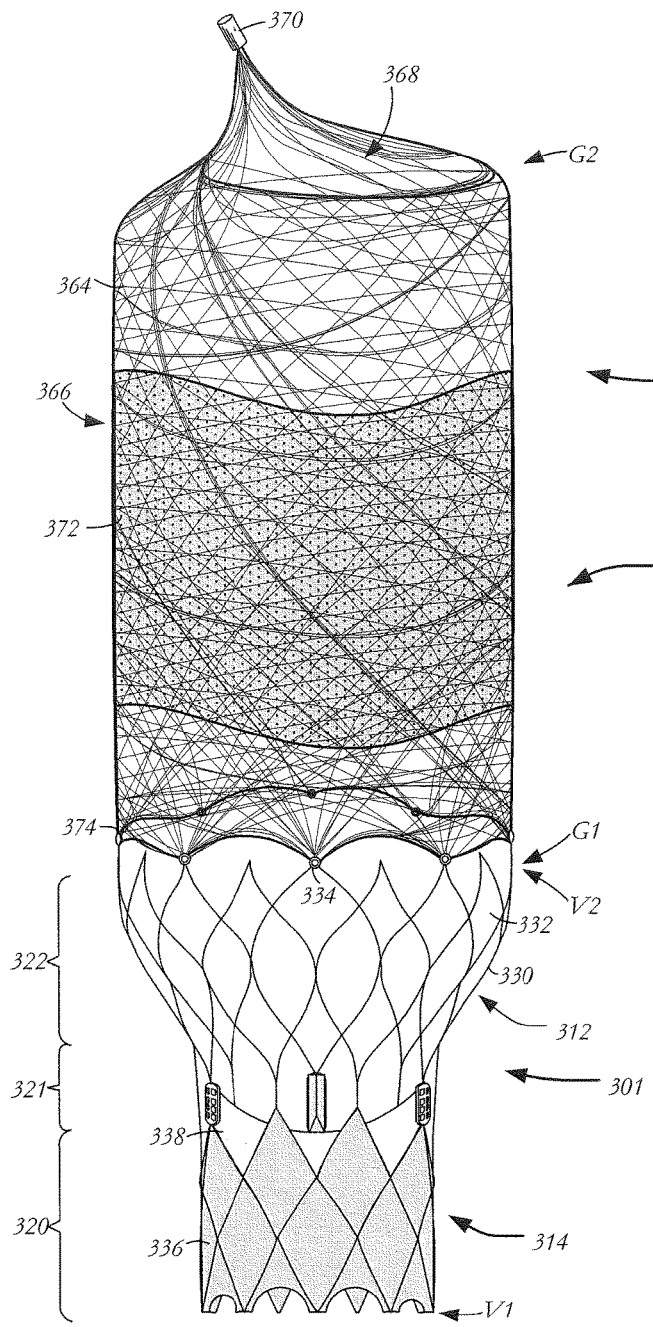
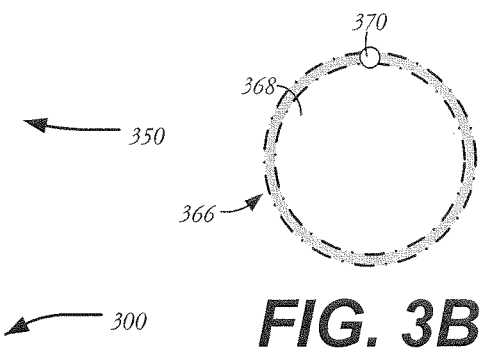
FIG. 3B
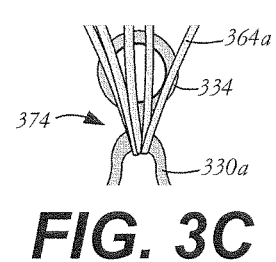
FIG. 3C
FIG. 3A

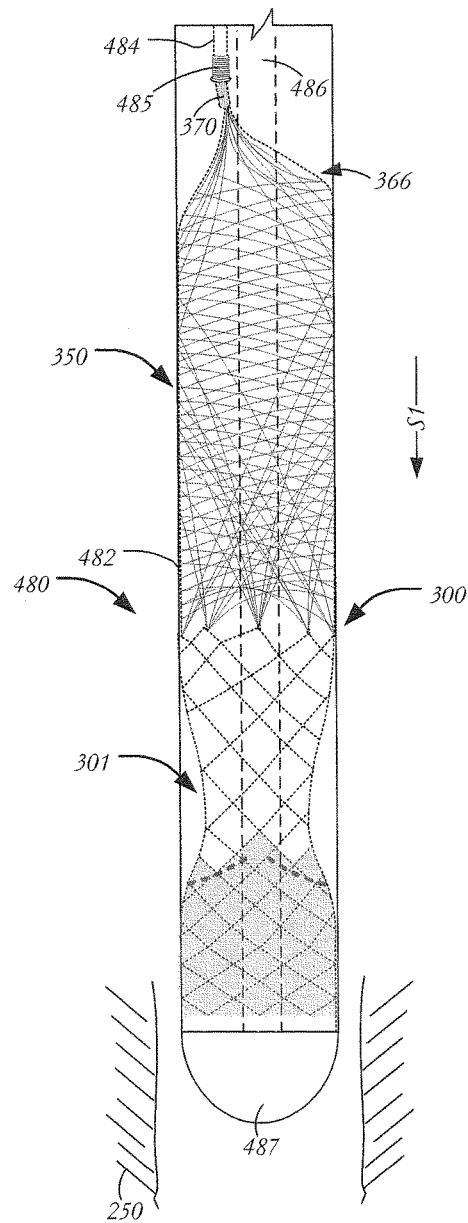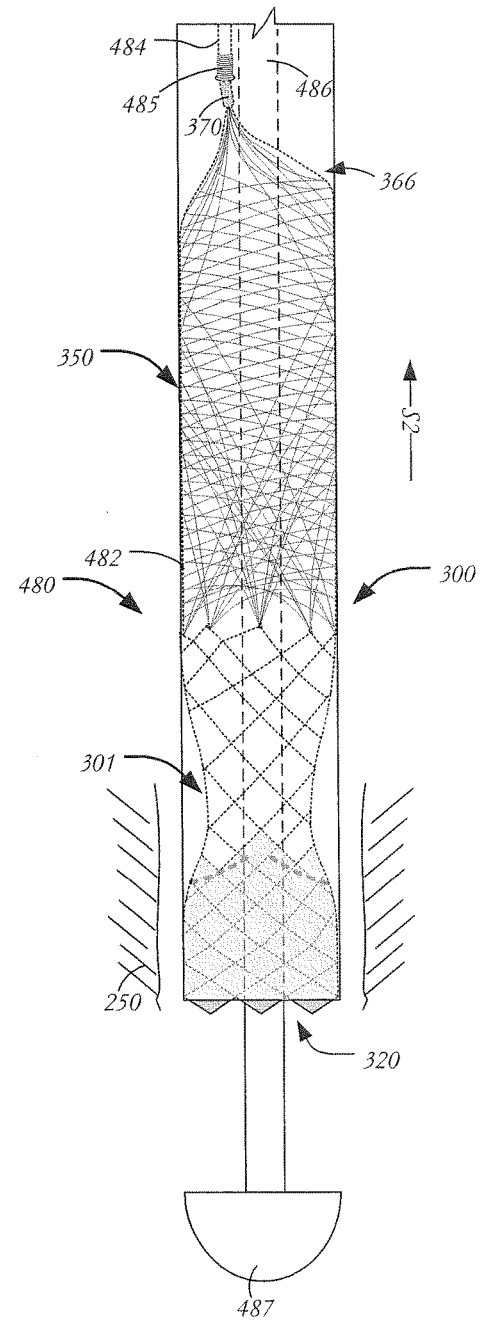
FIG. 5A  FIG. 5B

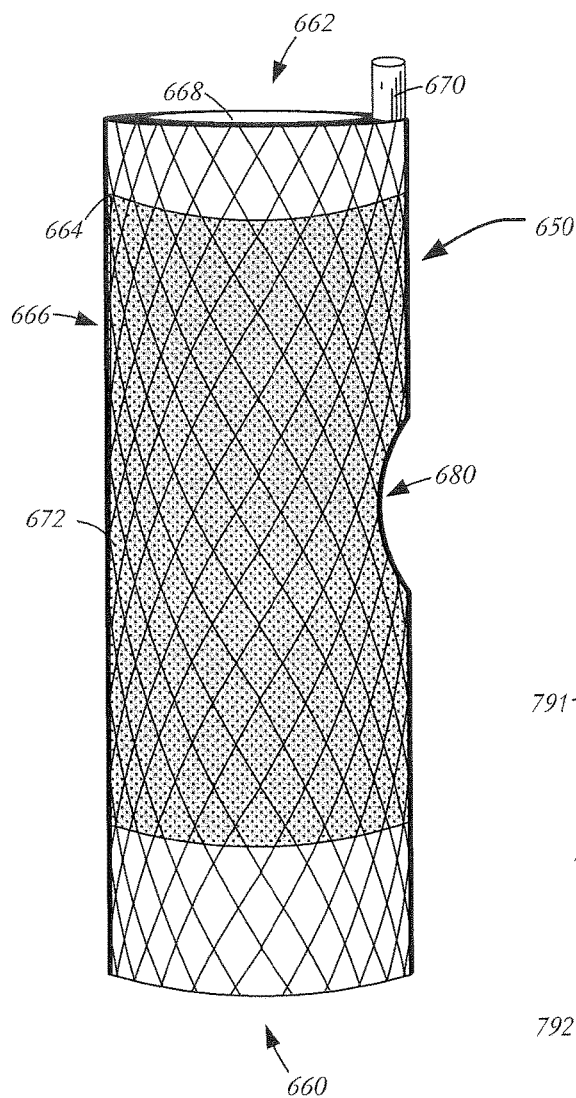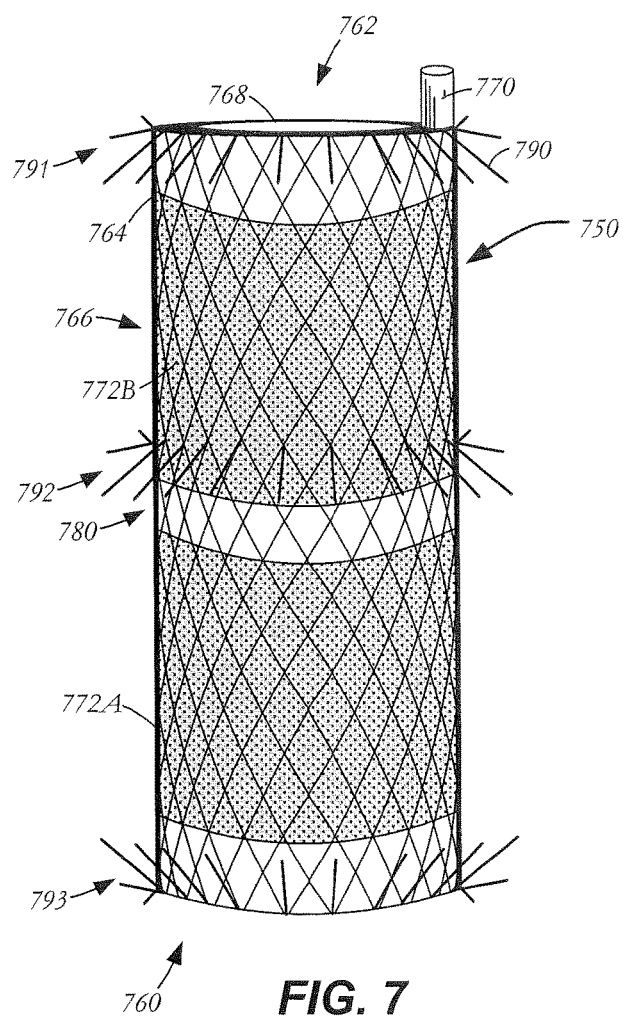
FIG. 6
FIG. 7

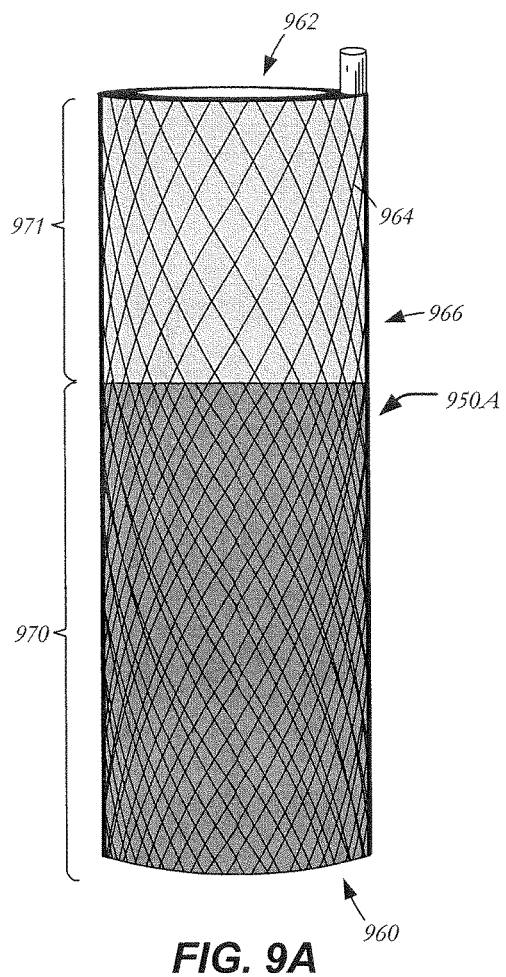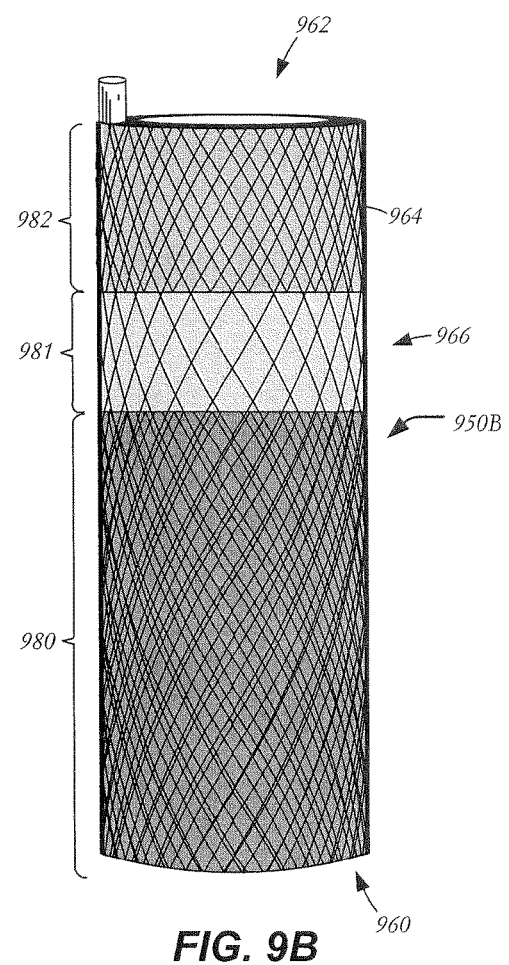
FIG. 9A
FIG. 9B

RECAPTURABLE VALVE-GRAFT COMBINATION AND RELATED METHODS

CROSS-REFERENCE TO RELATED APPLICATIONS

The present application claims the benefit of the filing date of U.S. Provisional Patent Application No. 62/132,609 filed Mar. 13, 2015, the disclosure of which is hereby incorporated herein by reference.

BACKGROUND OF THE INVENTION

The present disclosure relates to heart valve replacement and, in particular, to collapsible prosthetic heart valves. More particularly, the present disclosure relates to collapsible prosthetic heart valves that may be repositioned during the deployment procedure and which address other abnormalities in the heart.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

SUMMARY OF THE INVENTION

In some embodiments, a therapeutic device may include a prosthetic heart valve including a collapsible and expandable stent having an aortic section and an annulus section, and a valve assembly disposed within the annulus section of the stent. The valve assembly may include a plurality of leaflets. A graft may be coupled to the aortic section of the collapsible and expandable stent. The graft may have a body and at least one lining disposed on the body and defining a lumen therethrough.

In some embodiments, a method of implanting a therapeutic device comprising delivering the therapeutic device in a collapsed condition to the native valve annulus, the therapeutic device may include: (i) a prosthetic heart valve including a collapsible and expandable stent having an aortic section and an annulus section, and a valve assembly disposed within the annulus section of the stent, the valve assembly including a plurality of leaflets, and (ii) a graft coupled to the aortic section of the collapsible and expandable stent, the graft having a body and at least one lining disposed on the body and defining a lumen therethrough, at least partially deploying the prosthetic heart valve at the native valve annulus, and deploying the graft downstream from the prosthetic heart valve in the direction of blood flow.

BRIEF DESCRIPTION OF THE DRAWINGS

Various embodiments of the present disclosure will now be described with reference to the appended drawings. It is to be appreciated that these drawings depict only some embodiments of the disclosure and are therefore not to be considered limiting of its scope.

FIG. 3A is a highly schematic side elevational view of one embodiment of a therapeutic device including a prosthetic heart valve and a graft;

FIG. 3B is a highly schematic top view of a graft showing the positioning of a securing means on the graft body;

FIG. 3C is an enlarged highly schematic side view wire strands of a graft coupled to a retaining element of a prosthetic heart valve;

FIGS. 5A-E are highly schematic side views showing one method of delivering and deploying the therapeutic device of FIG. 3A within the native valve annulus;

FIG. 6 is a highly schematic perspective view of one embodiment of a therapeutic device having a lateral passageway;

FIG. 7 is a highly schematic perspective view of one embodiment of a therapeutic device having stabilizing wires;

FIGS. 9A and 9B are highly schematic side elevational views of embodiments of therapeutic devices including grafts having portions with varying densities;

DETAILED DESCRIPTION

Figure 1:
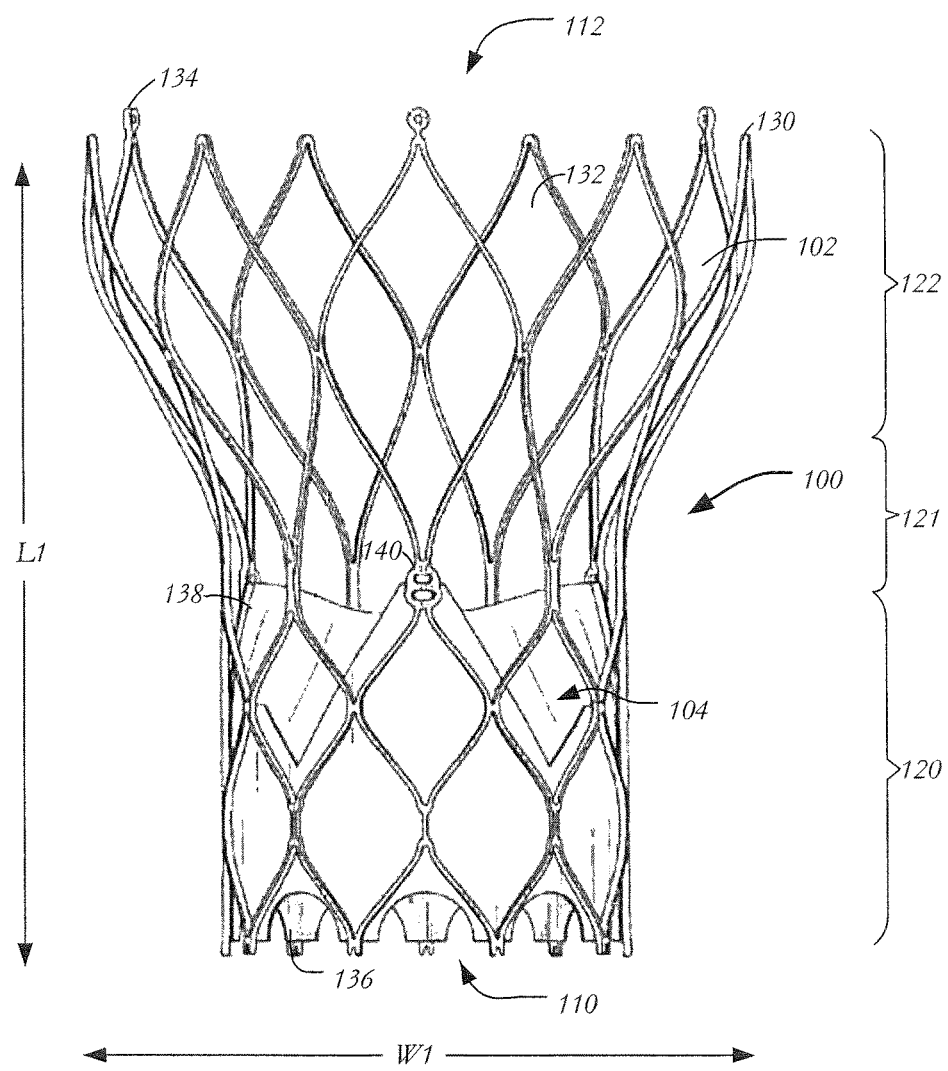
FIG. 1 is a side elevational view of a conventional prosthetic heart valve.

The clinical success of self-expanding valves may be dependent on accurate deployment and anchoring. Inaccurate deployment and anchoring of the valve increases risks, such as those associated with valve migration, which may cause severe complications due to the obstruction of the left ventricular outflow tract. Inaccurate deployment and anchoring may also result in the leakage of blood between the implanted heart valve and the native valve annulus, commonly referred to as perivalvular leakage (also known as "paravalvular leakage"). In aortic valves, this leakage enables blood to flow from the aorta back into the left ventricle, reducing cardiac efficiency and putting a greater strain on the heart muscle.

Moreover, anatomical variations from one patient to another may cause a fully deployed heart valve to function improperly, requiring removal of the valve from the patient. Removing a fully deployed heart valve increases the length of the procedure as well as the risk of infection and/or damage to heart tissue. Thus, methods and devices are desirable that would reduce the need to remove a prosthetic heart valve from a patient.

Once a self-expanding valve has been fully deployed, it expands to a diameter larger than that of the sheath that previously contained the valve in the collapsed condition, making resheathing impossible, or difficult at best. Additionally, while replacing a diseased valve, it would be beneficial to address other deficiencies and/or abnormalities in the heart to avoid multiple procedures. For example, in some cases, it may be helpful to treat a localized abnormal dilation of a lumen and more particularly, aneurysms, fistulas, legions or the like in certain blood vessels simultaneously while replacing the function of a native heart valve.

Thus, it would be helpful to have a resheathable device that replaces the function of a native heart valve (e.g., an aortic valve) while simultaneously treating abnormal dilations. There therefore is a need for further improvements to the devices, systems, and methods for transcatheter delivery of collapsible integrated prosthetic heart valves and grafts, and in particular, self-expanding prosthetic heart valves and graft combinations. Among other advantages, the present disclosure may address one or more of these needs.

There is a need for further improvements to the devices, systems, and methods for transcatheter delivery and positioning of collapsible prosthetic heart valves. Specifically, there is a need for devices, systems, and methods for accurately implanting a prosthetic heart valve and grafts, alone or in combination. Among other advantages, the present disclosure may address one or more of these needs.

As used herein, the term "proximal," when used in connection with a therapeutic device, a prosthetic heart valve or a graft, refers to the end of the device closest to the heart when the device is implanted in a patient, whereas the term "distal," when used in connection with such devices, refers to the end of the device farthest from the heart when the device is implanted in a patient. Also, as used herein, the words "substantially," "approximately," "generally" and "about" are intended to mean that slight variations from absolute are included within the scope of the structure or process recited.

FIG. 1 shows a collapsible stent-supported prosthetic heart valve 100 including a stent 102 and a valve assembly 104 as is known in the art. The prosthetic heart valve 100 is designed to replace a native tricuspid valve of a patient, such as a native aortic valve. It should be noted that while the devices disclosed herein are described predominantly in connection with their use with a prosthetic aortic valve and a stent having a shape as illustrated in FIG. 1, the valve could be a bicuspid or other valve, such as the mitral valve, and the stent could have different shapes, such as a flared or conical annulus section, a less-bulbous aortic section, and the like, and a differently shaped transition section.

The expandable stent 102 of prosthetic heart valve 100 may be formed from biocompatible materials that are capable of self-expansion, such as, for example, shape memory alloys, such as the nickel-titanium alloy known as "nitinol," or other suitable metals or polymers. Stent 102 extends in a length direction L1 from proximal or annulus end 110 to distal or aortic end 112, and includes annulus section 120 adjacent proximal end 110, transition section 121, and aortic section 122 adjacent distal end 112. Annulus section 120 has a relatively small cross-section in the expanded condition, while aortic section 122 has a relatively large cross-section in the expanded condition. Preferably, annulus section 120 is in the form of a cylinder having a substantially constant diameter along its length. Transition section 121 may taper outwardly from annulus section 120 to aortic section 122. Each of the sections of stent 102 includes a plurality of struts 130 forming cells 132 connected to one another in one or more annular rows around the stent. For example, as shown in FIG. 1, annulus section 120 may have two annular rows of complete cells 132 and aortic section 122 and transition section 121 may each have one or more annular rows of partial cells 132. Cells 132 in aortic section 122 may be larger than cells 132 in annulus section 120. The larger cells in aortic section 122 better enable prosthetic valve 100 to be positioned in the native valve annulus without the stent structure interfering with blood flow to the coronary arteries. Each of cells 132 has a length in length direction L1 of the stent and a width W1 in a perpendicular direction.

Stent 102 may include one or more retaining elements 134 at distal end 112 thereof, retaining elements 134 being sized and shaped to cooperate with female retaining structures (not shown) provided on a deployment device. The engagement of retaining elements 134 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Valve assembly 104 of prosthetic heart valve 100 preferably is positioned in annulus section 120 of stent 102 and secured to the stent. Valve assembly 104 includes cuff 136 and a plurality of leaflets 138 which collectively function as a one-way valve by coapting with one another. As a prosthetic aortic valve, valve 100 has three leaflets 138.

Although cuff 136 is shown in FIG. 1 as being disposed on the luminal or inner surface of annulus section 120, it is contemplated that cuff 136 may be disposed on the abluminal or outer surface of annulus section 120 or may cover all or part of either or both of the luminal and abluminal surfaces. Both cuff 136 and leaflets 138 may be wholly or partly formed of any suitable biological material or polymer such as, for example, polytetrafluoroethylene (PTFE).

Leaflets 138 may be attached along their belly portions to cells 132 of stent 102, with the commissure between adjacent leaflets 138 attached to a commissure feature 140. As can be seen in FIG. 1, each commissure feature 140 may lie at the intersection of four cells 132, two of the cells being adjacent one another in the same annular row, and the other two cells being in different annular rows and lying in end-to-end relationship. Preferably, commissure features 140 are positioned entirely within annulus section 120 or at the juncture of annulus section 120 and transition section 121. Commissure features 140 may include one or more eyelets which facilitate the suturing of the leaflet commissure to stent 102.

Prosthetic heart valve 100 may be used to replace a native aortic valve, a surgical heart valve or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into a patient using a transfemoral, transapical, transseptal or any other percutaneous approach. Once the delivery device has reached the target site, the user may deploy prosthetic heart valve 100. Upon deployment, prosthetic heart valve 100 expands so that annulus section 120 is in secure engagement within the native aortic annulus. When prosthetic heart valve 100 is properly positioned inside the heart, it works as a one-way valve, allowing blood to flow from the left ventricle of the heart to the aorta, and preventing blood from flowing in the opposite direction.

Figure 2:
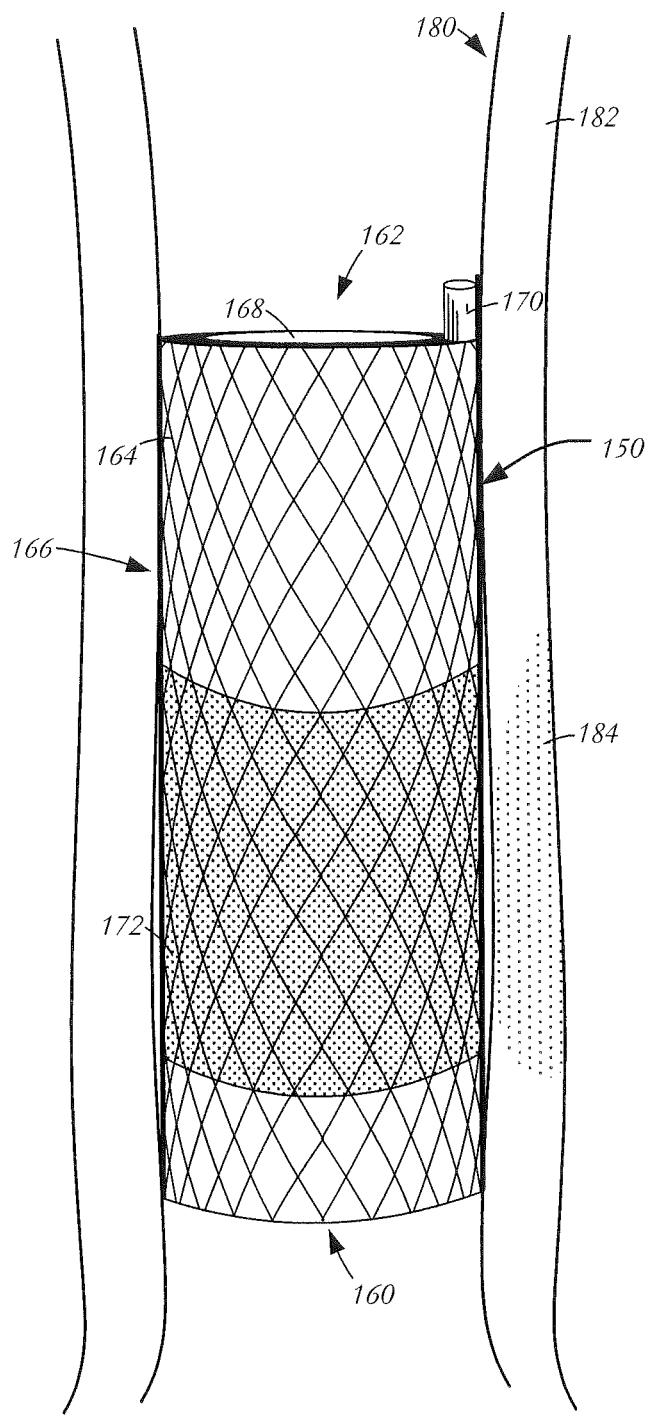
FIG. 2 is a side elevational view of a graft having a body and a lining.

In addition to replacing the function of a native heart valve with prosthetic valves, grafts may be used to treat aneurysms and fistulas. FIG. 2 illustrates one example of graft 150, which is a stent-like structure sized for placement in a blood vessel. Graft 150 extends between proximal end 160 and distal end 162 and is composed of a series of metal wires or strands 164 woven or braided into a generally tubular mesh body 166 defining a longitudinally-extending lumen 168 therethrough. The ends of strands 164 may be held together by securing means 170 at distal end 162 as shown to maintain integrity of mesh body 166. Alternatively or in addition to securing means 170, ends of strands 164 may be welded, heat treated, or otherwise secured to prevent unraveling. Securing means 170 may be adapted for coupling to an end of a cable or a catheter for delivery to a pre-selected site within the patient as will be discussed in greater detail below.

Mesh body 166 may be formed from a plurality of strands 164 having a predetermined relative orientation between the strands in a fully expanded condition. Generally, mesh body 166 includes two sets of substantially parallel, generally spiraling and overlapping strands 164, with the strands of one set having a "hand," i.e., a direction of spiral, opposite that of the other set. This type of mesh body may also be referred to as a tubular braid. It will be understood that strands 164 may also be braided to form a body having two or more layers of strands, with one layer overlying the other.

The pitch of strands 164 (i.e., the angle defined between the turns of the wire and the longitudinal axis of the mesh body 166) and the pick of the body 166 (i.e., the number of turns per unit length), as well as some other factors, such as the number of wires employed in a tubular braid, the size or diameter of each wire in the braid, and the diameter of the braid may be selected to produce an appropriate body 166 for a given usage. For example, the greater the pick and pitch of the braid, and hence, the greater the density of the wire strands in the body 166, the greater will be the stiffness of the body. Likewise, the greater the diameter of each wire of the braid, the greater will be the stiffness of body 166. Having a greater wire density will also provide the device with a greater wire surface area, which will generally enhance the tendency that fibrin forms on the surface of the device. This thrombogenicity can be abated by a coating of a thrombolytic agent, or by a coating of a lubricious, antithrombogenic compound. When using a tubular braid to form a device of the present disclosure, a tubular braid of about 45 mm in diameter (or other suitable diameter that correlates to a size of the patient's aortic vessel) having approximately 72 braided wires is suitable for fabricating the body of the device. Of course, those skilled in the art will appreciate that the number of braided wires may be increased substantially to more than 144 braided wires and the diameter of each wire may be increased or decreased depending upon the size of the vessel in which the graft is to be positioned.

Strands 164 of body 166 may be manufactured from so-called shape memory alloys. Thus, graft 150 may be manufactured from a shape memory alloy, wherein the shape of the device may be dependent on temperature or may be manufactured to be independent of temperature. When manufacturing body 166 from shape memory alloys to be independent of temperature changes, a preferred configuration can be fixed by heating the material above a certain phase change transition temperature to induce a change in the phase of the material. When the alloy is cooled back down, the alloy will "remember" the shape it was in during the heat treatment and will tend to assume that configuration independent of temperatures less than the heat treatment temperature, unless constrained from so doing.

By way of example, suitable wire strand materials may include a cobalt-based low thermal expansion alloy referred to in the field as ELGELOY, nickel-based high temperature high-strength "superalloys" (including nitinol) commercially available from, for example, Haynes International under the trade name HASTELLOY, nickel-based heat treatable alloys sold under the name INCOLOY by International Nickel, and a number of different grades of stainless steel. Wire strands 164 may also be made from nitinol or nitinol alloys, which are very elastic and are said to be "super elastic" or "pseudo elastic." This elasticity allows a device of the disclosure to return to a preset configuration after deployment. Additionally, nitinol may be helpful in constructing a graft that is more flexible to pass through sharp curvatures in the body (e.g., the aortic arch), and may also be able to provide a lower delivery profile. Thus, using any of these materials, body 166 may be formed of a collapsible and expandable material that allows it to be crimped to a small diameter for delivery and to expand during deployment.

After manufacturing body 166 as desired, a lining 172 may be added to a portion of body 166 on either the luminal or the abluminal surface of the body. Alternatively, body 166 may be formed of multiple layers and lining 172 may be disposed between any two layers of the body. Lining 172 may form a conduit for blood flow and may also promote healing. In at least some examples, lining 172 may include polyester, polytetrafluoroethylene ("PTFE"), ultra-high molecular weight polyethylene and/or other suitable polymeric or fabric materials, such as those used in cuff 136 of heart valve 100.

As shown in FIG. 2, graft 150 may be deployed within vessel wall 182 of blood vessel 180. Specifically, graft 150 may be deployed at the location of weakened portion 184 of blood vessel 180. If weakened portion 184 is left untreated, pulsing blood pressure may expand the weakened portion and eventually rupture the blood vessel. Instead, blood flowing through lumen 168 of body 166 reduces the pulsing of blood against the weakened portion 184 of blood vessel 180.

FIG. 3A illustrates therapeutic device 300 intended to treat both native valve and blood vessel deficiencies. Therapeutic device 300 includes prosthetic heart valve 301, which extends between proximal end V1 and distal end V2 and may include all the features of prosthetic heart valve 100 of FIG. 1. Prosthetic heart valve 301 generally includes stent 312 and valve assembly 314 disposed within stent 312. Stent 312 includes annulus section 320, transition section 321 and aortic section 322, and is formed of a plurality of struts 330 forming cells 332. Struts 330 at distal end V2 may terminate in one or more retaining elements 334, which may be similar to retaining elements 134 from FIG. 1 or slightly modified to allow coupling of a graft to stent 312. Additionally, valve assembly 314 includes cuff 336 and leaflets 338.

As shown in FIG. 3A, therapeutic device 300 further includes graft 350 coupled to distal end V2 of prosthetic heart valve 301. Graft 350 may include all the features of graft 150 of FIG. 2. Graft 350 extends between proximal end G1 and distal end G2 and is composed of a series of metal strands 364 woven into a generally tubular mesh body 366 having a longitudinally-extending lumen 368 therethrough. The ends of strands 364 may be held together by securing means 370, such as a clamp as shown, at distal end G2 as shown or by any other suitable means such as welding, heat treatment, or the like. As schematically shown in FIG. 3B, securing means 370 may be disposed off-center of body 366 so that the entrance to lumen 368 is unobstructed (e.g., securing means 370 may be disposed on the circumference of body 366). It will be understood that multiple securing means 370 may be used and that their positions may vary. For example, securing means 370 may be disposed on both the proximal end G1 and the distal end G2 of graft 350, or multiple securing means 370 may be disposed at either or both ends of graft 350. Further still, a clampless embodiment may instead include welded strand ends and other means of securement to a deployment device. Lining 372 may be disposed on at least a portion of body 366 on the luminal surface, the abluminal surface or both surfaces. Lining 372 may be similar to any of the examples described above with reference to lining 172.

Proximal end G1 of graft 350 may be coupled to distal end V2 of prosthetic heart valve 301 as shown. In this example, selected strands 364a of body 366 are coupled to retaining elements 334 of prosthetic heart valve 301 (FIG. 3C). Strands 364a may be wrapped around or tied to certain struts 330a of aortic section 322 as shown. Each group of strands 364a attached to a strut may form a leg 374 of body 366. In at least some examples, legs 374 may be formed by welding or crimping strands 364a together into a grouping and then separately attaching the grouping to a strut via suturing, bonding, crimping, welding or any other suitable method. Body 366 may include any number of legs 374. In at least some examples, body 366 includes the same number of legs as there are retaining elements on prosthetic heart valve 301. In at least some other examples, body 366 may include as many as twelve legs or as few as one leg 374. Alternatively, legs 374 may be attached to other portions of the prosthetic heart valve 301 (e.g., to other struts 330 in aortic section 322 or transition section 321). Depending on the length of legs 274, a gap may be defined between graft 350 and prosthetic heart valve 301, which may be a source of leakage. The amount of leakage can be minimized by attaching fabric in this area. Alternative methods for minimizing the leakage between graft 350 and prosthetic heart valve 301 will be described below.

Figure 4A:
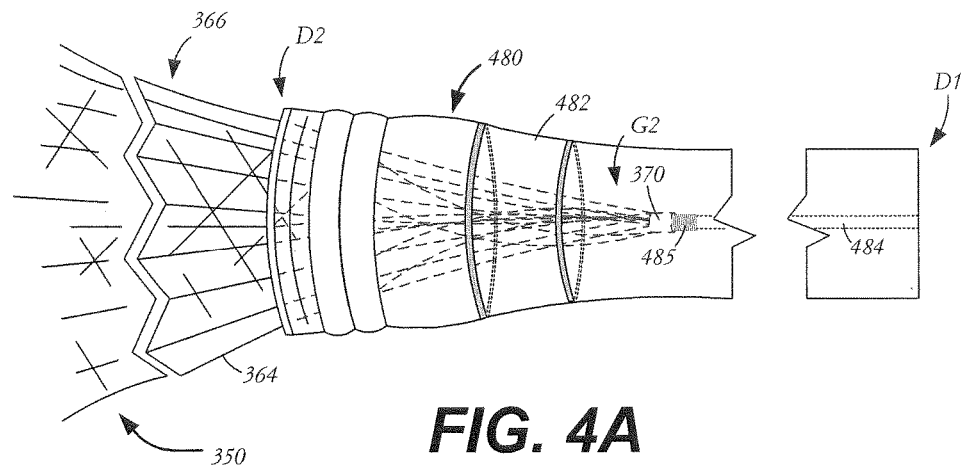
FIGS. 4A and 4B are highly schematic side views showing methods of loading a therapeutic device into a delivery device.
Figure 4B:
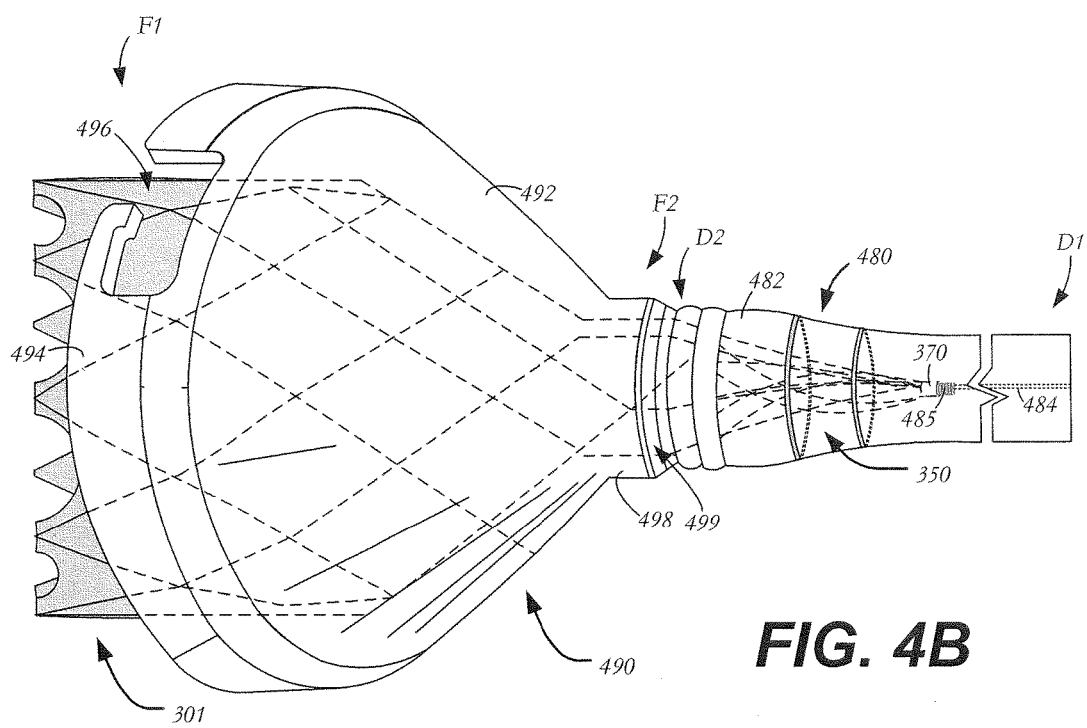

FIGS. 4A and 4B illustrate methods of loading therapeutic device 300 into delivery device 480. Delivery device 480 includes outer sheath 482, inner shaft 484 and connector 485, and generally extends between trailing end D1 and leading end D2. Delivery device 480 may optionally include an atraumatic distal tip (not shown) coupled to a core (also not shown). Outer sheath 482 may be slightly tapered from leading end D2 to trailing end D1 as shown, or may be substantially cylindrical. Inner shaft 484 may be disposed within outer sheath 482 may be slidable relative thereto. The leading end of inner shaft 484 may include connector 485 configured to mate with securing means 370 at distal end G2 of graft 350. In some examples, connector 485 may be a male connector configured to couple, lock or screw into a female connector of securing means 370. In other examples, connector 405 may be a female connector configured to mate with a male connector of securing means 370. With connector 485 properly mated with securing means 370, inner shaft 484 may be retracted toward trailing end D1 to pull graft 350 within outer sheath 482.

Due to the construction of body 366, graft 350 may be sufficiently pliable to pull into outer sheath 482 without requiring great force. In some examples, it may be helpful to use an additional compression member 490 to help crimp prosthetic heart valve 301. Such a compression member may be used alone or in conjunction with a support member such as that described in U.S. patent application Ser. No. 13/558, 942, filed Jul. 26, 2012, titled "SYSTEM FOR LOADING A COLLAPSIBLE HEART VALVE," the disclosure of which is hereby incorporated herein by reference in its entirety as if entirely set forth. Compression member 490 includes funnel 492 having a substantially frusto-conical shape with a large diameter at a first open end F1 and a smaller diameter at a second open end F2. The interior diameter of the funnel 492 decreases progressively from the first end F1 to the second end F2. Compression member 490 is preferably made of a substantially rigid material, and may be wholly or partly made of a transparent plastic, such as polycarbonate or acrylic, to allow viewing of the valve 301 during loading.

Compression member 490 may further include an annular rim 494 extending from the first end F1 of funnel 492 for joining the compression member to a support member (not shown). Rim 494 may include a plurality of slots 496 disposed around its outer periphery for mating with projections on the support member. While the drawings show slots 496 that are substantially P-shaped, the slots may have any other shapes suitable for mating with the projections on the support member to securely assemble the support member to compression member 490.

Compression member 490 also may include a tubular extension 498 projecting from second end F2 of funnel 492. Tubular extension 498 has an opening 499 therethrough in communication with the interior of funnel 492. Opening 499 is sized and shaped to be inserted into the outer sheath 482 of delivery device 480. The cross-section of the tubular extension 498 is preferably substantially circular, but may be oblong, oval, elliptical, or polygonal. With compression member 490 coupled to the leading edge outer sheath 482 of delivery device 480, inner shaft 484 may then be coupled to connector 485 to load therapeutic device 300 into delivery device 480. Prosthetic heart valve 301 may be urged through funnel 492 and tubular extension 498 of compression member 490 with or without the use of a support member to load therapeutic device 300 into delivery device 480.

A method of delivering and implanting therapeutic device 300 will now be described with reference to FIGS. 5A-E. Delivery system 480 may be used to deliver therapeutic device 300 to a native valve annulus and an adjacent vessel and to deploy same, and may generally include outer sheath 482, inner shaft 484 with a connector 485, core 486, and atraumatic tip 487 coupled to core 486. Alternatively, the inner shaft 484 and connector 485 may be designed as multiple female retainer coupling structures (not shown) for mating with each of the distal legs of a graft. Outer sheath 482 may be slidable relative to inner shaft 484 and core 486. For the sake of clarity, certain features of therapeutic device 300, such as the commissure features of the heart valve and the lining of the graft, are not shown.

Figure 5C:
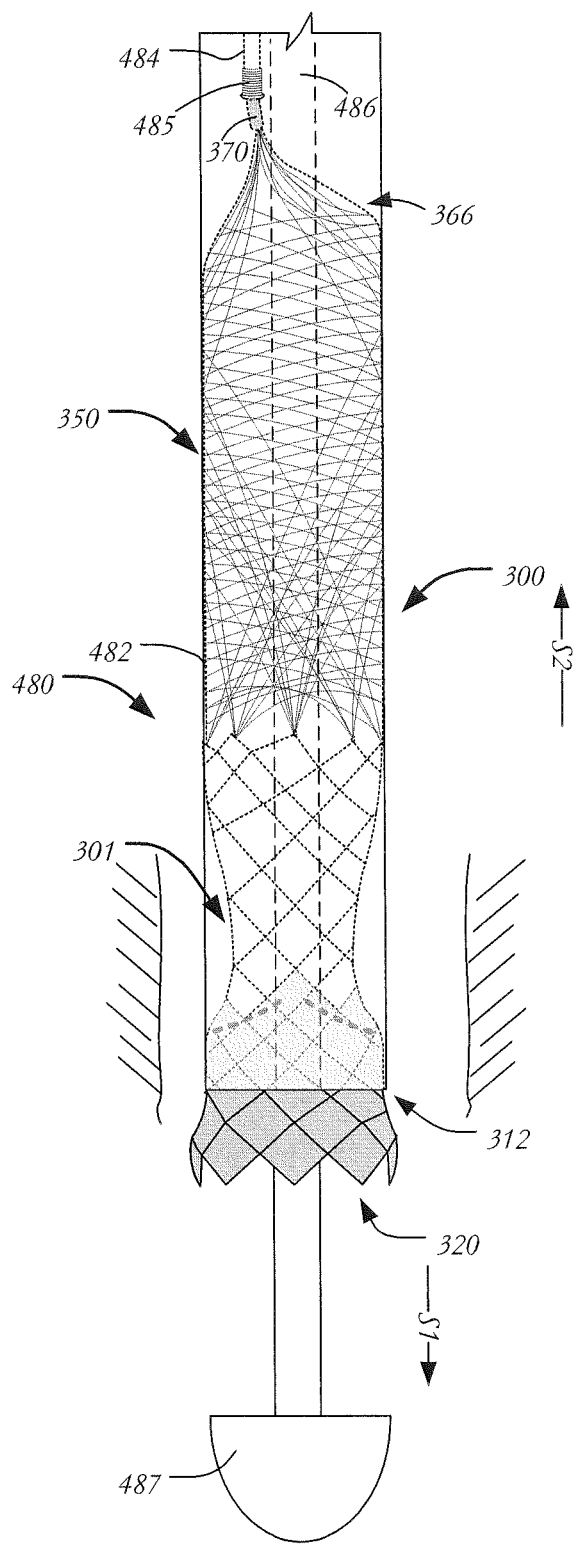

Therapeutic device 300 may be disposed within outer sheath 482 in a collapsed condition (FIG. 5A). By collapsing all sections of heart valve 301 and graft 350, therapeutic device 300 may be delivered to native valve annulus 250 using a minimally invasive delivery system 480 without increasing the radius of outer sheath 482. A large delivery system may be incapable of being passed through the patient's vasculature, whereas a delivery system for a heart valve with a smaller crimp profile may be easier to navigate through a patient's body and may also reduce the operation time. In the example shown in FIGS. 5A-E, delivery system 480 is delivered from the aorta toward the left ventricle as indicated by arrow S1, although other approaches are feasible. If therapeutic device 300 or delivery system 480 includes echogenic materials, such materials may be used to guide delivery system 480 to the appropriate position using the assistance of three-dimensional echocardiography to visualize the therapeutic device within the patient. Alternative visualization techniques known in the art are also contemplated herein.

When delivery system 480 has reached the proper location (e.g., atraumatic tip 487 is just past native valve annulus 250), atraumatic tip 487 may be advanced slightly in the direction of arrow S1 toward the left ventricle by pushing core 486 toward atraumatic tip 487 while holding outer sheath 482 in place, which serves to decouple atraumatic tip 487 from sheath 482 (FIG. 5B). Outer sheath 482 may then be retracted in the direction of arrow S2 toward the aorta. As seen in FIG. 5B, with outer sheath 482 slightly retracted, heart valve 301 begins to emerge from the sheath, beginning with annulus section 320. As sheath 482 is further retracted in the direction of arrow S2, more of annulus section 320 of stent 312 is exposed (FIG. 5C). This may continue until annulus section 320 is fully exposed and the remaining portions of stent 312 are still disposed within outer sheath 482. While heart valve 301 is partially deployed (e.g., only annulus section 320 is outside sheath 482, and heart valve 301 is not fully detached from delivery system 480), if it appears that heart valve 301 needs to be recaptured and redeployed due to, for example, improper positioning or orientation, outer sheath 482 may be slid over core 486 in the direction of arrow S1 to recollapse heart valve 301 within sheath 482. This partial deployment procedure may be repeated until heart valve 301 is properly positioned.

Figure 5D:
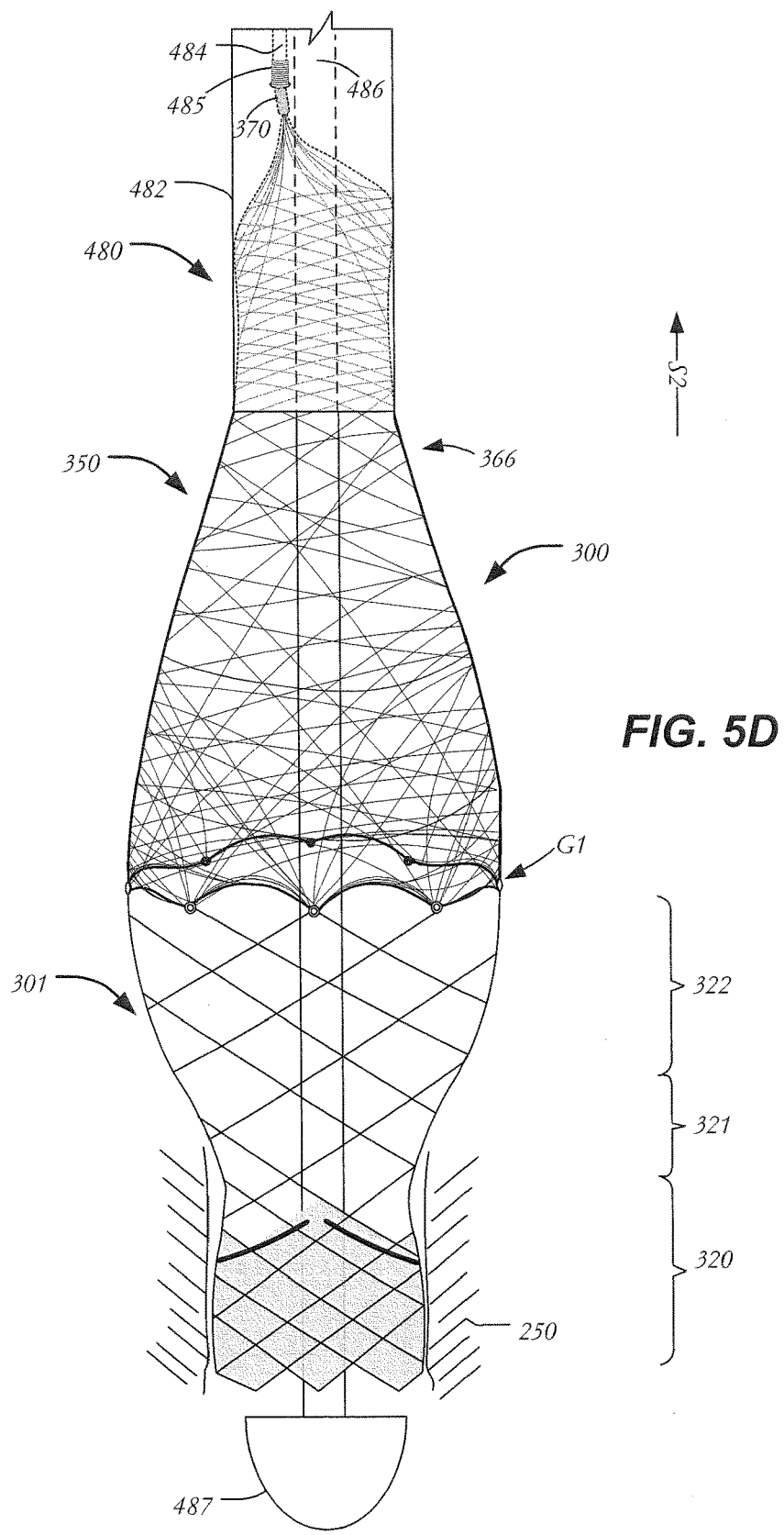

After ascertaining proper positioning, sheath 482 may be further withdrawn to expose transition section 321 and finally aortic section 322 of heart valve 301, thereby releasing all of the heart valve from the sheath while retaining a portion of graft 350 within the sheath (FIG. 5D). As seen in FIG. 5D, heart valve 301 expands to fill native valve annulus 250. Once heart valve 301 is fully deployed, graft 350 may begin to be exposed, beginning with proximal end G1, by continuing to retract outer sheath 482 in the direction of arrow S2. Graft 350 may begin to foreshorten in length as it radially expands. Optionally, inner shaft 484 may be advanced (in the direction of S1) while pulling back outer sheath 482 (in the direction of S2) to compensate for the shortening of graft 350 during deployment. In some examples, a gear or series of gears (not shown) may be used to automatically advance inner shaft 484 in the direction of arrow S1 while outer sheath 482 is being pulled back in the direction of arrow S2. After therapeutic device 300 is fully deployed, inner shaft 484 may be decoupled from securing means 370, for example, by twisting connector 485 with respect to securing means 370 to decouple the pair and release therapeutic device 300 from delivery system 480. It will be appreciated that the proper placement and functioning of graft 350 may be adjusted at any time prior to decoupling securing means 370 from connector 485. For example, if graft 350 is not in the correct position, body 366 may be resheathed and moved to a different location or orientation with the aid of visualization techniques, and redeployed in the appropriate position and/or orientation.

Figure 5E:
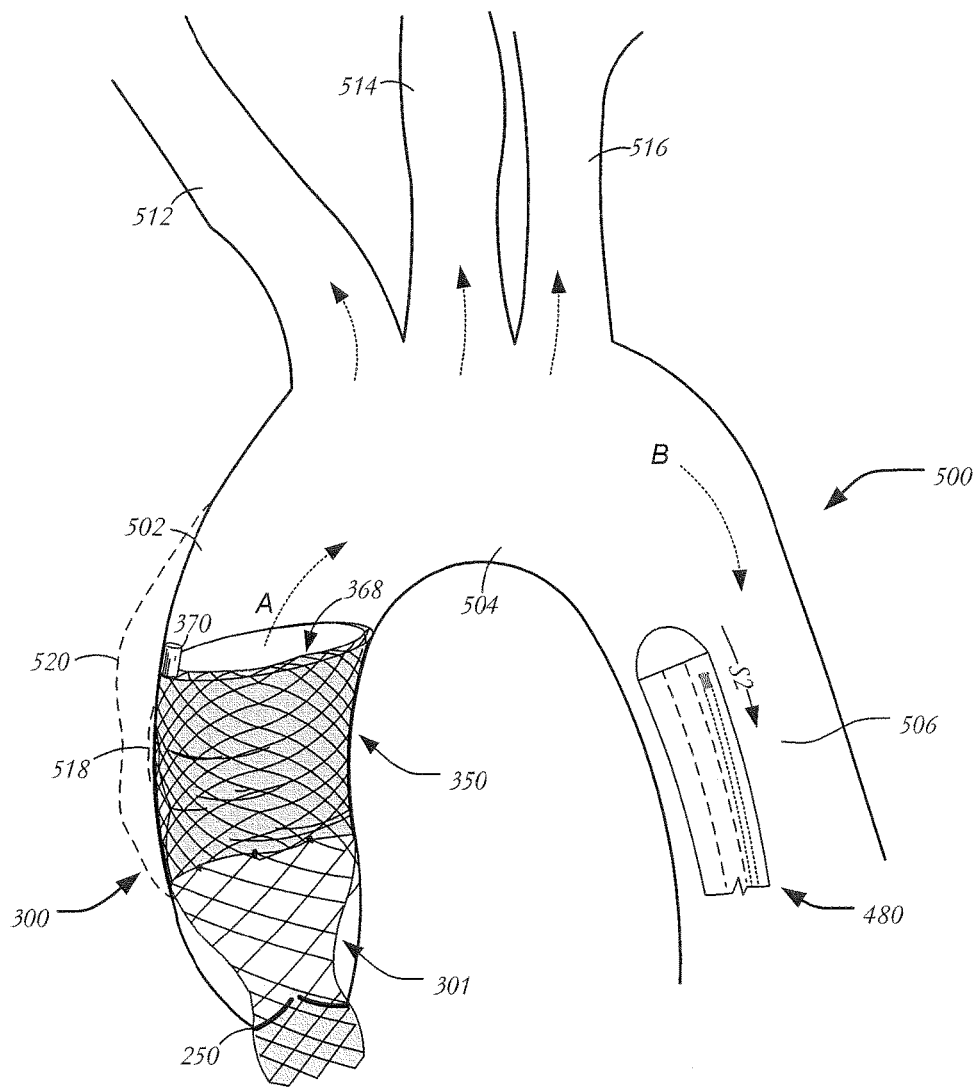

FIG. 5E illustrates therapeutic device 300 after full deployment in vivo. Aorta 500, the largest artery in the body, originates from the left ventricle (not shown) and extends down to the abdomen. Blood flows as indicated by arrow "A" from the left ventricle, through the aortic valve (not shown), through the ascending aorta 502 to the aortic arch 504, which is disposed between ascending aorta 502 and descending aorta 506. Branching from aortic arch 504 are three major arteries: brachiocephalic artery 512, which supplies blood to the right arm and the head and neck, left common carotid artery 514, which supplies blood to the head and neck, and left subclavian artery 516, which supplies blood to the left arm. Blood from ascending aorta 502 not passing through one of these three arteries continues down the descending aorta 506 as shown by arrow "B." In the instant case, the wall of ascending aorta 502 has a damaged portion 518 that has weakened and begun to bulge. If left untreated, portions of ascending aorta 502 may bulge outwardly to condition 520, and possibly rupture. Instead, therapeutic device 300 has been deployed to replace the function of the native aortic valve with prosthetic heart valve 301, and to relieve blood pressure at damaged portion 518 of ascending aorta 502 via graft 350. As shown in FIG. 5E, securing means 370 of graft 350 is disposed adjacent one wall of ascending aorta 502 and lumen 368 allows the flow of blood through ascending aorta 502 in the natural direction of flow as indicated by arrow "A." With therapeutic device 300 properly functioning, delivery device 480 may be removed from the body through descending aorta 506 in the direction S2.

The use of therapeutic device 300 allows the simultaneous treating of both a vessel abnormality via graft 350 and a diseased or nonfunctional heart valve via prosthetic heart valve 301. Thus, for candidates suffering from both conditions, the number of procedures is reduced as therapeutic device 300 allows implantation of a single device to address both conditions. Additionally, because therapeutic device 300 allows both prosthetic heart valve 301 and graft 350 to be delivered together, only a single delivery device is needed for completing the procedure. In practice, the simultaneous use of two distinct delivery devices, one for a graft, and a second for a prosthetic heart valve, may not be feasible due to space constraints, and no conventional delivery system is robust enough to be used for both a prosthetic heart valve and a graft. Thus, therapeutic device 300 shortens the operative time and reduces the chance of infection as well as other risk factors. Additionally, without being bound by any particular theory, it is believed that graft 350 and prosthetic heart valve 301 may aid each other in anchoring by providing a large surface area of contact with the native anatomy (i.e. a larger landing zone). Thus, proper anchoring of prosthetic heart valve 301 may play a role in keeping the graft in the proper location near an weakened vessel wall and graft 350 may help in avoiding prosthetic heart valve prolapse.

It will be appreciated that graft 350 may be modified in several ways to improve performance and/or to tailor the graft for a specific application. FIG. 6 shows a first variation of a graft having additional features relating to blood flow. Graft 650 may be a stent-like structure sized for placement in a blood vessel in a manner similar to graft 150 and may extend between proximal end 660 and distal end 662. Graft 650 includes a series of metal strands 664 woven into a generally tubular mesh body 666 defining a longitudinally-extending lumen 668 therethrough. Strands 664 may be held together by securing means 670 as previously described, and lining 672 may be disposed on a portion of the luminal surface of body 666.

The main difference between graft 650 and graft 150 described above is the inclusion of lateral aperture 680. As shown in FIG. 6, aperture 680 is formed through body 666 and lining 672, allowing lateral flow out from lumen 668. Aperture 680 may be useful for applications in which a longer graft is needed to bolster a vessel, while directing sufficient blood flow to an adjacent vessel. For example, graft 650 may be disposed in the ascending aorta, while directing blood flow through aperture 680 to any one of the brachiocephalic, carotid, or left subclavian arteries. It will be appreciated that multiple apertures 680 may be formed in graft 650 to direct blood flow to multiple branch arteries and may be disposed at any location along graft 650 between proximal end 660 and distal end 662.

Aperture 680 may be disposed substantially perpendicular to lumen 668 and may be formed by forming a complete graft 650 and then laser cutting a portion of body 666 and lining 672 to form the aperture. Alternatively, a lining 672 with a precut aperture may be coupled to body 666 to form aperture 680. Aperture 680 may be formed by forming an opening in lining 670 with or without additional modification to body 666.

Alternatively, two or more linings 672 may be disposed on body 666, the linings being longitudinally spaced apart to define a passageway therebetween. One such example of a graft having two linings is shown in FIG. 7. Graft 750 extends between proximal end 760 and distal end 762 and includes strands 764, body 766, lumen 768, securing means 770 and first and second linings 772A, 772B. Passageway 780 is defined between linings 772A, 772B and may allow blood to follow therethrough between lining 772,772B to side branches. Graft 750 further includes a plurality of stabilizing wires 790 arranged in circumferential first, second, and third rings 791, 792, 793, with first ring 791 being disposed adjacent distal end 762, third ring 793 being disposed adjacent proximal end 760 and second ring 792 being arranged intermediate first and third rings 791,793, preferably approximately halfway between first and third rings 791,793. Stabilizing wires 790 may be configured to radially project from body 766 to secure graft 750 to a blood vessel, such as the ascending aorta, for example. Stabilizing wires 790 may be more rigid or less compliant than wires which form body 766. Additionally, stabilizing wires 790 may be formed of a spring-loaded and/or shape memory material. It will be appreciated that any number of rings 791 may be utilized, and that each ring may include any number of stabilizing wires 790. For example, only a single ring 791 may be disposed on body 766, while other examples employ multiple rings. Stabilizing wires 790 may automatically expand upon deployment from a deployment device or may be manually actuated by a delivery system. It will be appreciated that, as used herein, the term "ring" does not necessarily imply a continuous structure but refers only to the placement of one or more stabilizing wires around a perimeter.

Figure 8:
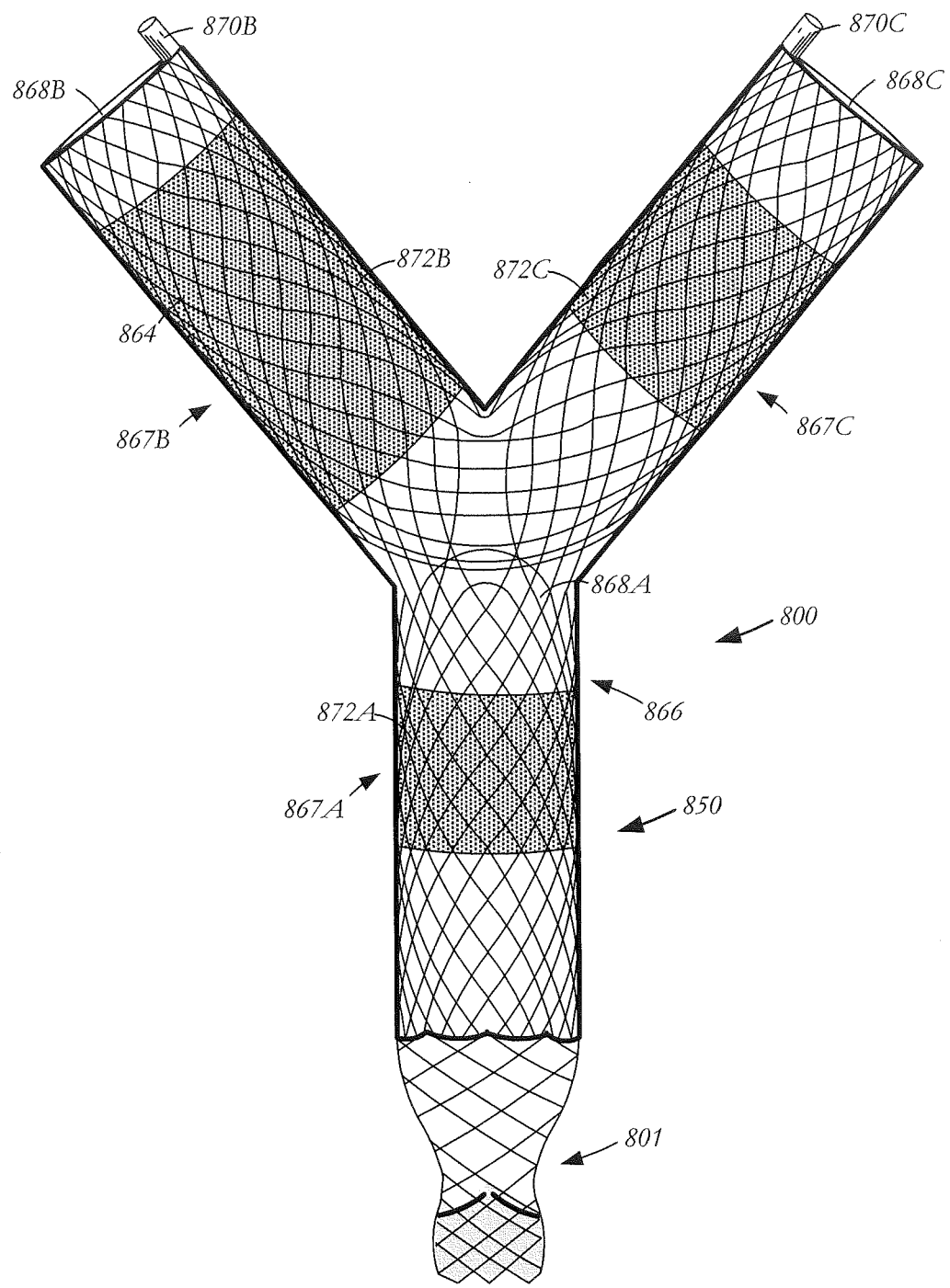
FIG. 8 is a highly schematic perspective view of one embodiment of a therapeutic device having a multi-branch graft.

FIG. 8 illustrates therapeutic device 800, which includes prosthetic heart valve 801 coupled to a multi-branch graft 850. Graft 850 generally includes a plurality of strands 864 forming a body 866 composed of three branches 867A-C. Each of branches 867A-C defines a lumen 868A-C extending through its center. As seen in FIG. 8, first branch 867A is attached at one end to prosthetic heart valve 801 and bifurcates at the other end to form second and third branches 867B,867C. Lumens 868A-C are all in communication with one another so that blood flowing through first lumen 868A continues through second and third lumens 868B,868C. Two securing means 870B,870C are disposed on second and third branches 867B,867C, respectively to aid in delivery and deployment. Specifically, second and third branches 867B, 867C may be brought together and collapsed onto each other until they are substantially parallel and securing means 870B,870C may be coupled to complementary structure on a delivery device. Delivery may continue as describe above, with prosthetic heart valve 801 being delivered first, followed by first branch 867A, and then either of second and third branches 867B,867C as desired. Each of branches 867A-C further includes a respective lining 872A-C disposed on its abluminal surface, the linings being of different sizes and being disposed at different locations on each of the branches. Multi-branch graft 850 may be used to treat multiple arteries prone to aneurysms. It will be understood that the shapes and sizes of the branches 867A-C may be modified. Additionally, the number of branches may also be varied and may range from three to five branches as desired. With multiples branches, aneurysm may be treated in multiple blood vessels, such as for example the brachiocephalic artery and the common carotid artery. Additionally, other features may be combined with the branching concept. For example, apertures as discussed above may be formed in any or all of the branches and linings may be disposed on any combination of luminal and/or abluminal surfaces of any of the branches.

FIGS. 9A and 9B illustrate two other variations of grafts in which the density of the braided wire has been modified. In a first variation, graft 950A extends between proximal end 960 and distal end 962 and includes wire 964 forming a body 966 having two portions with different wire densities (FIG. 9A). As shown, first portion 970 adjacent proximal end 960 has a higher density of wires than second portion 971 located adjacent distal end 962. A portion of greater wire density may be achieved by varying the pick and pitch of wire strands 964 as discussed above. In a second example, graft 950B includes three portions with different wire densities, first portion 980 disposed adjacent proximal end 960 having the greatest density, third portion 982 disposed adjacent distal end 962 having an intermediate density, and second portion 981 disposed between first portion 980 and second portion 982 having the lowest density. The different densities within graft 950B may reflect the different rigidities and wall thicknesses of vessels in the heart and may be useful in deploying the graft in tortuous environments. For example, a less dense intermediate portion 981 may be helpful in manipulating graft 950B and bending the graft at that location for traversing the aortic arch. The same or different linings may be disposed on each of the two portions 970, 971 of graft 950A, or three portions 980-982 of graft 950B. In some examples, different portions of graft 950B include different stiffness by way of different heat treatments. The sections may be heat treated differently by having thin and thick sections of the mold used for heating the Nitinol, or by heating up the different sections to different temperatures. Additionally, varying braiding methods and densities of the strands may be useful in defining zones of different stiffness.

Figure 10:
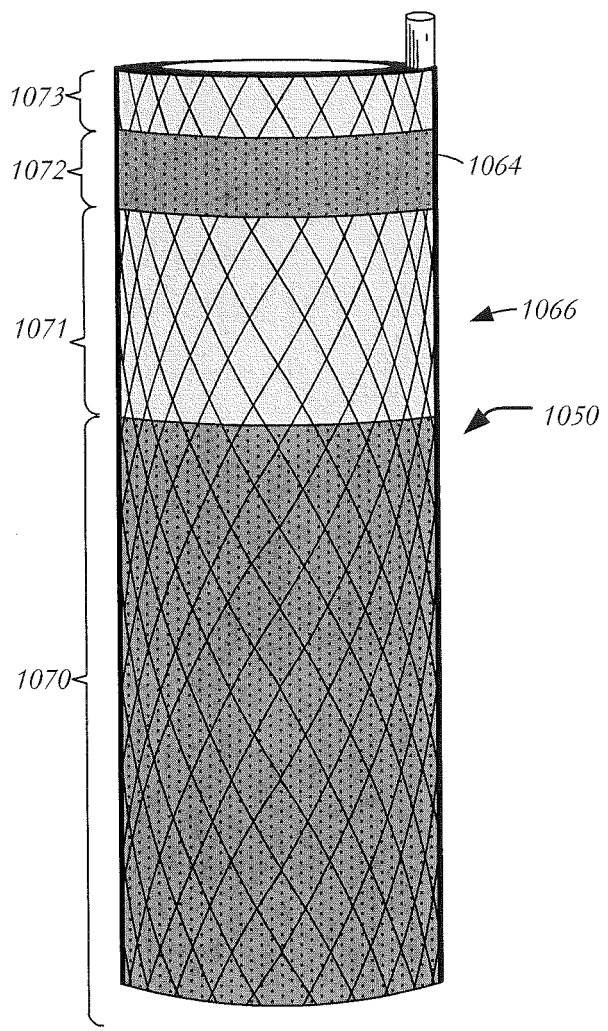
FIG. 10 is a highly schematic side elevational view of an embodiment of a therapeutic device including a graft having multiple linings.

As discussed above, the graft may include one or more linings depending on the application. For example, graft 1050 includes a body 1066 of strands 1064 and four different linings 1070-1073 (FIG. 10). Linings 1070-1073 may be formed of different materials and in different sizes and may be selected based on the desired application. For example, certain weakened portions may require a thick tissue lining, while others may be polymeric and chosen to aid in reducing the overall crimp profile of the device. Additionally, some of linings 1070-1073 may be disposed on the abluminal surface while others are formed on the luminal surface. In some examples, linings 1070-1073 may be coupled to one another by, for example, sewing their edges together or via lamination. Alternatively, linings 1070-1073 may overlap with one another in order to minimize leakage therethrough.

Figure 11:
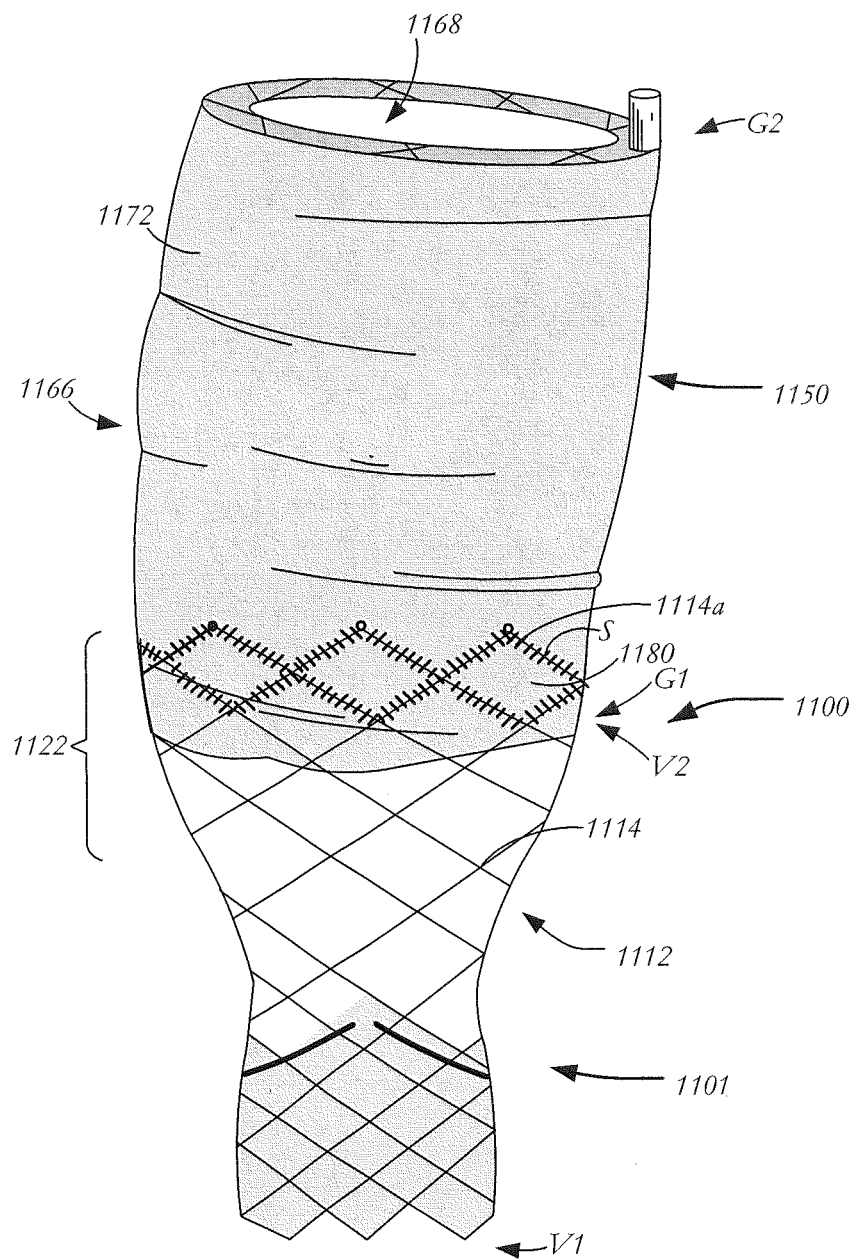
FIG. 11 is a highly schematic side elevational view of an embodiment of a therapeutic device including a graft having a sealing portion.

FIG. 11 illustrates another therapeutic device 1100 including prosthetic heart valve 1101 extending between proximal end V1 and distal end V2, heart valve 1101 including stent 1112 having struts 1114 and flared aortic section 1122. Therapeutic device 1110 further includes graft 1150 having body 1166 defining lumen 1168, with lining 1172 covering the abluminal surface of the body such that the strands of wires that form the body are not shown. The main difference between therapeutic device 1100 and the previously described examples is the spatial relationship between heart valve 1101 and graft 1150. Specifically, in this example a substantial portion of graft 1150 overlaps aortic section 1122 of stent 1112 to form sealing portion 1180, and lining 1172 of graft 1150 is coupled to struts 1114 such as struts 1114*a* of stent 1112 via sutures S. The purpose of sealing portion 1180 is to prevent blood from flowing around graft 1150 and instead force the blood to travel through lumen 1168. Because aortic portion 1122 of stent 1112 is flared, sealing portion 1180 may push against the walls of the ascending aorta or other vasculature structure as desired and prevent leakage around graft 1150 and heart valve 1101.

Figure 12A:
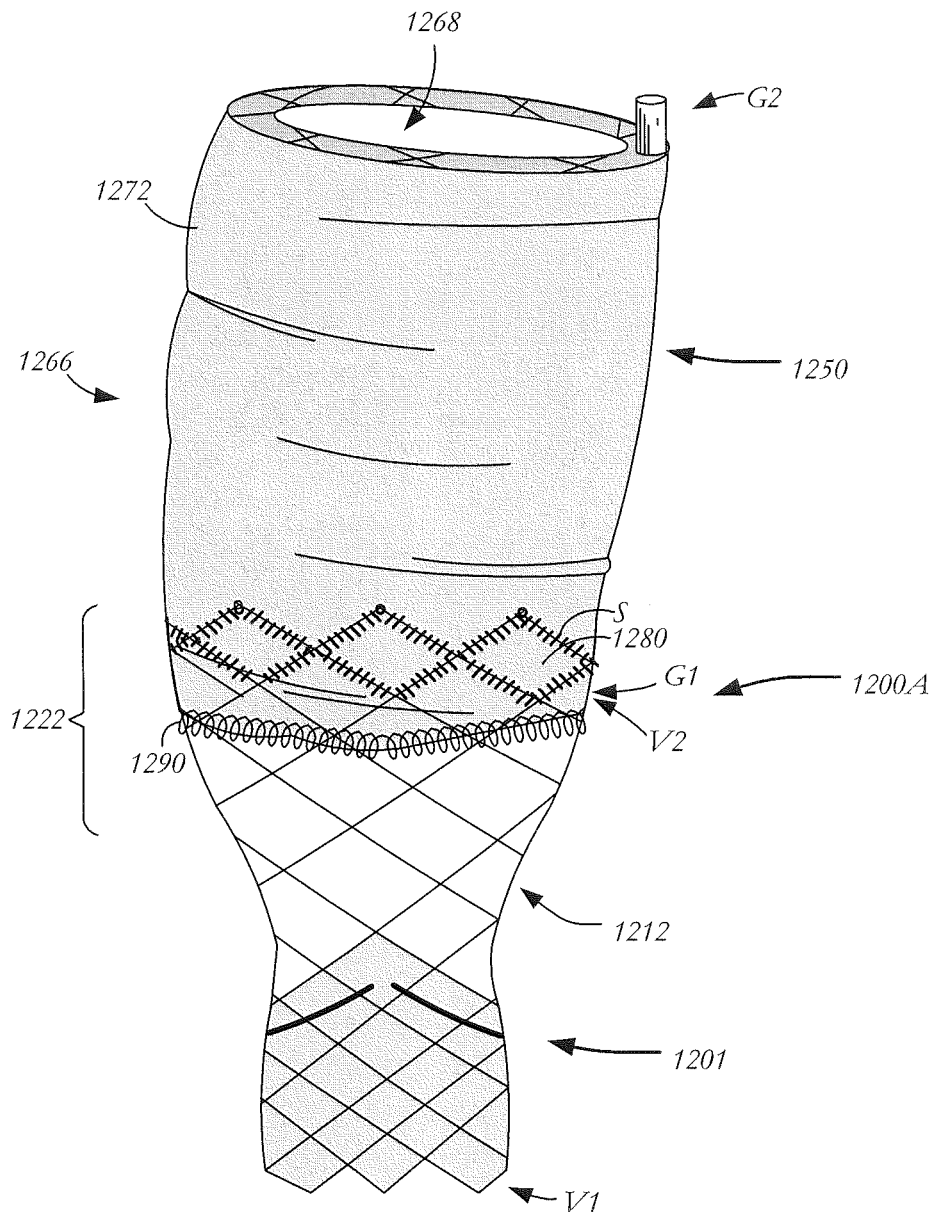
FIG. 12A is a highly schematic side elevational view of an embodiment of a therapeutic device including a sealing coil on one end of the graft.
Figure 12B:
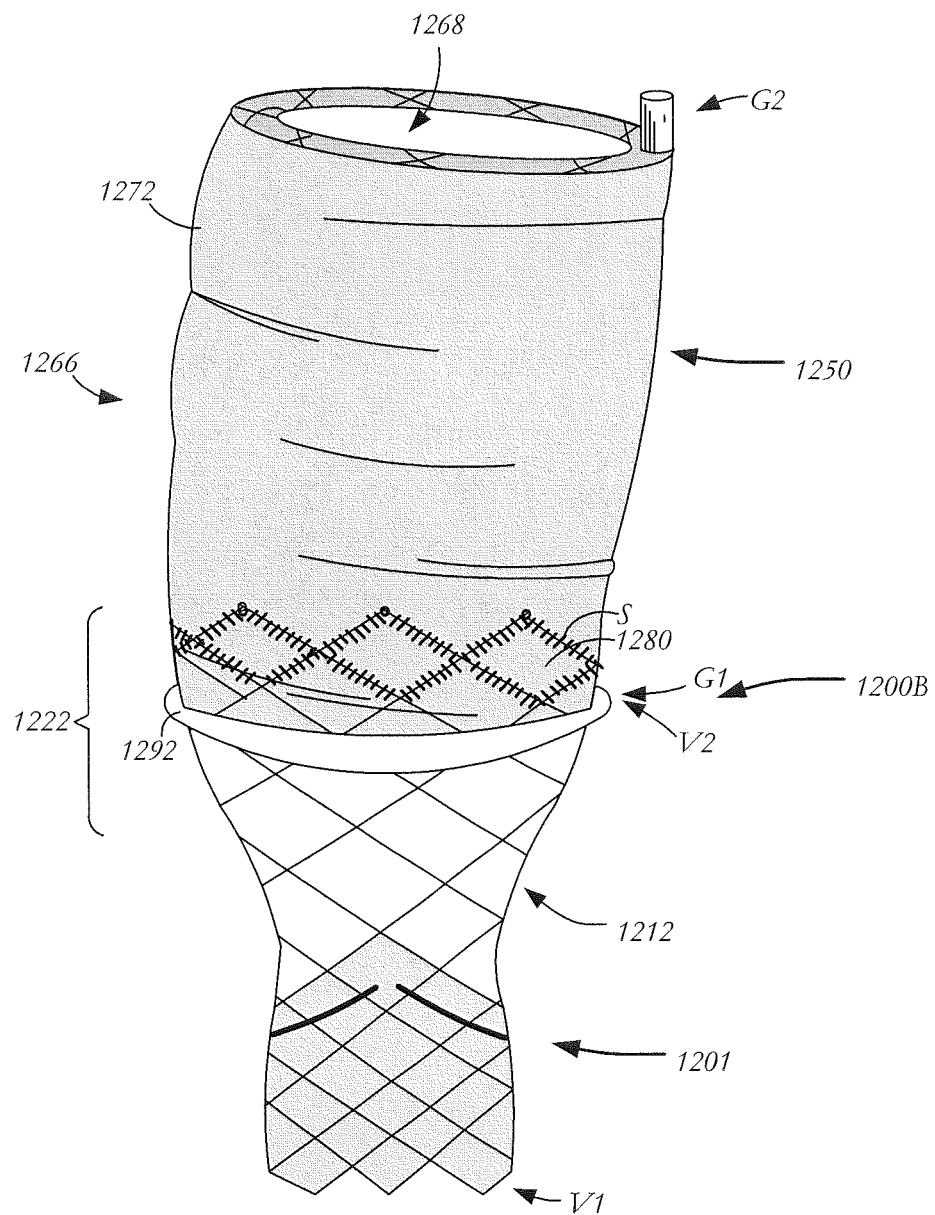
FIG. 12B is a highly schematic side elevational view of an embodiment of a therapeutic device including a sealing ring on one end of the graft.

The therapeutic devices as described herein may include additional features to increase the effectiveness of the graft sealing. FIGS. 12A and 12B, for example, show therapeutic devices 1200A and 1200B similar to therapeutic device 1100, but having additional sealing features. Like-numbered elements of FIGS. 12A and 12B correspond to like-numbered elements in FIG. 11, but are preceded by a "12" instead of an "11." For example, stent 1112 in FIG. 11 corresponds to stent 1212 of FIGS. 12A and 12B. In FIG. 12A, coil 1290 is added to therapeutic device 1200A to aid in sealing. Coil 1290 may include a shape-memory material such as a metal and may be configured to radially expand after deployment to push against the walls of the target vessel. Alternatively, thinner struts may be cut as a part of the stent. These thinner struts may be formed as curled up structures when the stent shape is formed using heat setting techniques. After deployment, the curled up structure may resume its shape, pushing against the walls of the target vessel. In some examples, as shown in FIG. 12A, coil 1290 is coupled to lining 1272 of graft 1250 adjacent proximal end G1 and is configured to push the edge of the lining radially outward to prevent leakage of blood around graft 1250 and heart valve 1201. Lining 1272 may be disposed over coil 1290 so that the coil pushes it outwardly against the vessel wall. Alternatively, coil 1290 may be threaded through lining 1272. Coil 1290 may also be wrapped with a separate lining made of fabric or other similar material. FIG. 12B illustrates a similar therapeutic device 1200B that includes an elastomeric ring 1292 for sealing graft 1250 against vascular tissue instead of coil 1290. Elastomeric ring 1290 may be formed as an O-ring and attached to proximal end G1 of graft 1250.

Figure 13:
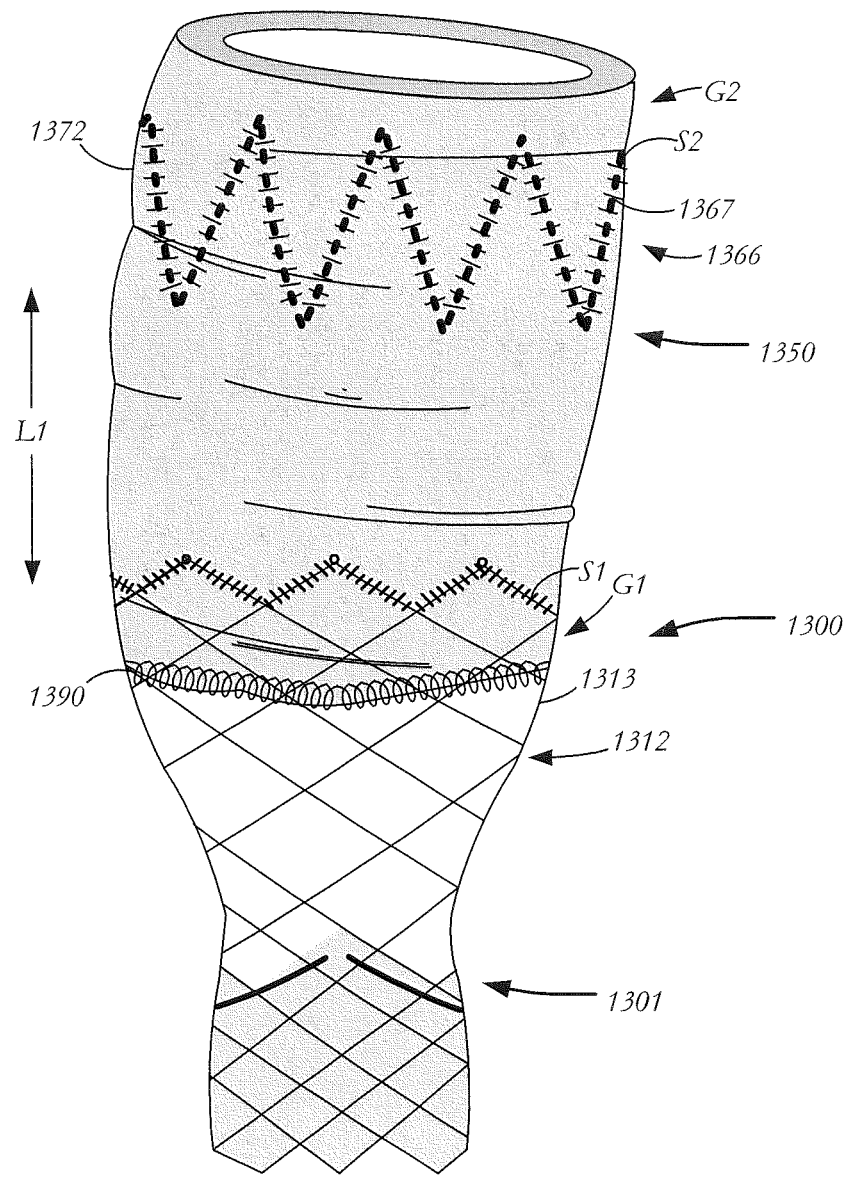
FIG. 13 is a highly schematic side elevational view of an embodiment of a therapeutic device including a graft having a metallic ring.

FIG. 13 illustrates another therapeutic device 1300 having heart valve 1301 and graft 1350. Heart valve 1301 has a stent 1312 similar to the heart valve stents described above. However, graft 1350 is different from the grafts described above in its construction. Rather than having a mesh body formed from intersecting wire strands, graft 1350 has a single anchoring ring 1366 formed of zigzagging struts 1367. Anchoring ring 1366 may be formed from the same or different materials than struts 1313 of stent 1312. In some examples, anchoring ring 1366 includes shape memory alloys, such as nitinol, other suitable metals or polymers, or combinations thereof. Similar to stent 1312, anchoring ring 1366 may be collapsible and expandable and configured to be introduced into the patient's body via a delivery device after being crimped down to a smaller diameter. It will be understood that examples having multiple anchoring rings are also possible.

As shown in FIG. 13, ring 1366 may be spaced from stent 1312 by a predetermined distance L1, distance L1 being selected based on the intended length of graft 1350. Lining 1372 may extend between proximal end G1 of graft 1350 and distal end G2 of graft 1350. At distal end G2, lining 1372 may be coupled to anchoring ring 1366. As shown, lining 1372 may be coupled to either the luminal or abluminal surface of stent 1312 with sutures S1, and to either the luminal or abluminal surface of ring 1366 via sutures S2. Lining 1372 may further be coupled to coil 1390, similar to coil 1290 of FIG. 12A, to aid in sealing the space between graft 1350 and the vessel wall at proximal end G1. Thus, a portion of graft disposed between stent 1312 and ring 1366 may be unsupported by any scaffolding or framing structure. However, when stent 1312 and ring 1366 are both properly deployed at predetermined locations, lining 1372 will extend between the two supporting structures to define the length of the graft.

Figure 14:
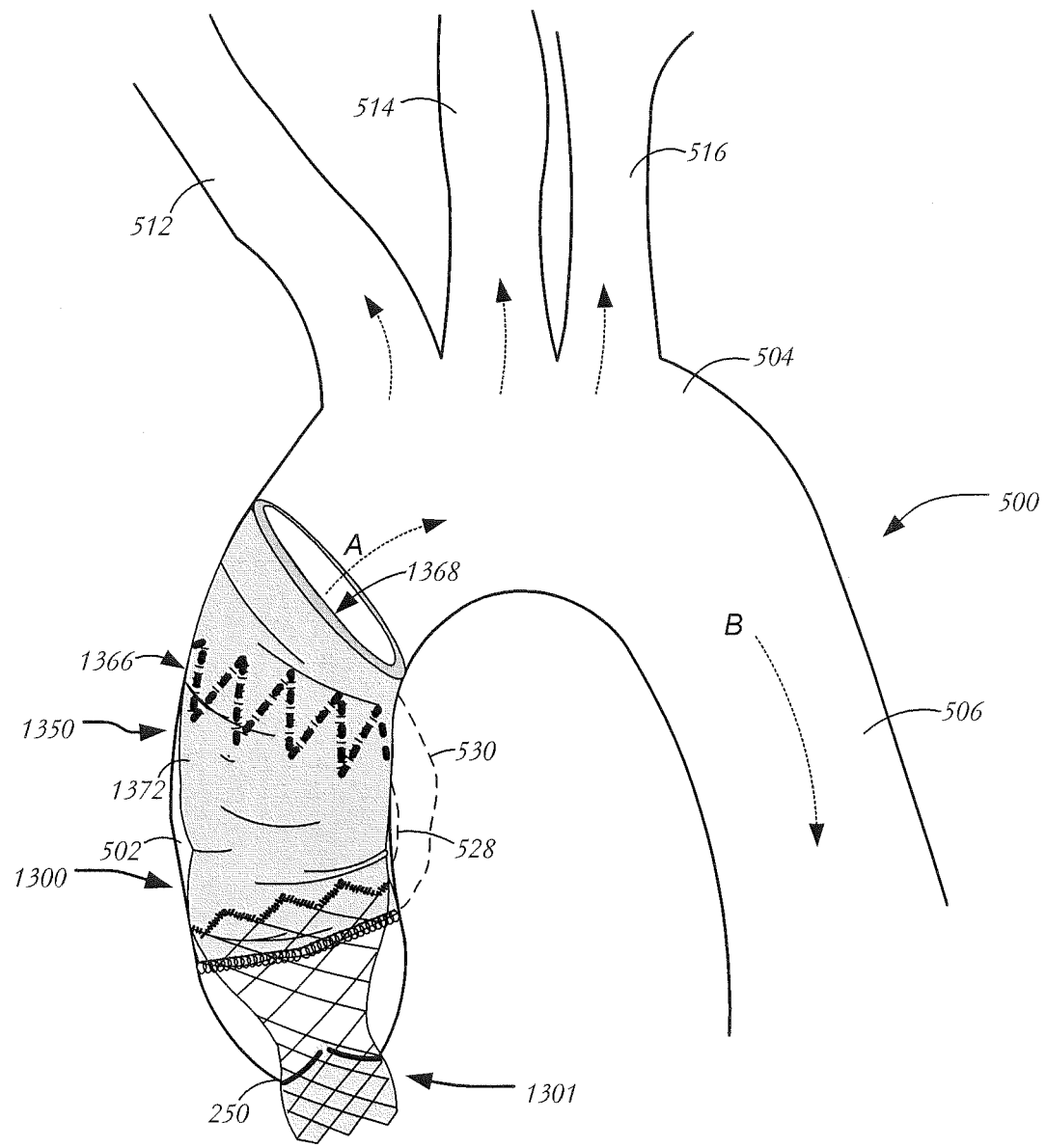
FIG. 14 is a highly schematic side elevational view of a therapeutic device including a graft having a metallic ring that has been implanted in the ascending aorta of a patient.

FIG. 14 illustrates therapeutic device 1300 after full deployment. In the instant case, damaged portion 528 of the wall of ascending aorta 502 has been weakened and has begun to bulge. If left untreated, portions of ascending aorta 502 may bulge out to condition 530, and possibly rupture. Instead, therapeutic device 1300 has been deployed to simultaneously replace the function of the native aortic valve with prosthetic heart valve 1301, and relieve blood pressure at damaged portion 528 via graft 1350, prosthetic heart valve 1301 and graft 1350 being useful for anchoring each other. As shown in FIG. 14, lumen 1368 has opened and blood may then travel through ascending aorta 502 in the natural direction of flow as indicated by arrow "A."

It will be appreciated that therapeutic device 1300 may be deployed in a manner similar to that described above. Specifically, prosthetic heart valve 1301 may first be partially deployed at native valve annulus 250, and, if necessary, resheathed, repositioned and redeployed until satisfactory functioning of heart valve 1301 is confirmed. With heart valve 1301 in place, coil 1390 or other coiled structures may be released, which allows the coil to expand as shown against a vessel wall. Once deployed, heart valve 1301 and coil 1390 may function as first anchors and allow the delivery device to be further retracted to stretch out graft 1350 along a portion of ascending aorta 502. Additionally, coil 1390 pushes lining 1372 out against the wall of ascending aorta 502 such that blood is prevented from flowing around graft 1350. More of graft 1350 may be unsheathed until ring 1366 is deployed, and expands functioning as a second anchor near distal end G2 of graft 1350. Securing means 1370 may then be released from the delivery device and the delivery device removed from the patient's body (not shown).

Although the devices herein have been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosures as defined by the appended claims.

In some embodiments, a therapeutic device, may include a prosthetic heart valve including a collapsible and expandable stent having an aortic section and an annulus section, and a valve assembly disposed within the annulus section of the stent, the valve assembly including a plurality of leaflets, and a graft coupled to the aortic section of the collapsible and expandable stent, the graft having a body and at least one lining disposed on the body and defining a lumen therethrough.

In some examples, the stent includes a plurality of struts defining a plurality of cells and the graft may be coupled to selected ones of the plurality of struts; and/or the stent further may include a plurality of retaining elements disposed in the aortic section and the graft is coupled to selected struts near the retaining elements; and/or the body may include a plurality of legs, each of the legs being coupled to one of the struts of the stent; and/or the at least one lining may be disposed on a luminal surface of the body; and/or the at least one lining may be disposed on an abluminal surface of the body; and/or the body may include a plurality of braided wire strands; and/or the wire strands include nitinol; and/or the graft may be collapsible and expandable and configured to fit within an artery; and/or the body may have a generally tubular sidewall with an aperture in the sidewall; and/or the graft further may include a plurality of radially extending stabilizing wires coupled to the body, the stabilizing wires being grouped to form at least one ring extending around a perimeter of the body; and/or the stabilizing wires may be grouped to form multiple rings extending around the periphery of the body, the rings being disposed at different axial positions on the graft; and/or the body may have a plurality of branches, each branch having a lumen in communication with lumens of others of the branches; and/or a first portion of the body may include a first density, and a second portion of the body has a density different from the first density; and/or the graft may include multiple linings disposed on the body, the linings being spaced from one another in a length direction of the graft; and/or the graft may include of the graft at least partially overlaps with the aortic section of the stent; and/or the device may further include a sealing structure coupled to the graft adjacent the aortic section of the prosthetic heart valve; and/or the sealing structure includes a coil disposed around a periphery of the body; and/or the body may include a collapsible and expandable metallic ring positioned at a spaced distance from the aortic section of the stent.

In some embodiments, a method of implanting a therapeutic device comprising delivering the therapeutic device in a collapsed condition to the native valve annulus, the therapeutic device may include: (i) a prosthetic heart valve including a collapsible and expandable stent having an aortic section and an annulus section, and a valve assembly disposed within the annulus section of the stent, the valve assembly including a plurality of leaflets, and (ii) a graft coupled to the aortic section of the collapsible and expandable stent, the graft having a body and at least one lining disposed on the body and defining a lumen therethrough, at least partially deploying the prosthetic heart valve at the native valve annulus, and deploying the graft downstream from the prosthetic heart valve in the direction of blood flow.

In some examples, the method of implanting a therapeutic device may further include repositioning the prosthetic heart valve until proper functioning of the valve assembly is confirmed prior to deploying the graft; and/or the step of deploying the graft may include deploying the graft in the ascending aorta.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A therapeutic device, comprising:
a prosthetic heart valve including a collapsible and expandable stent having an aortic section with a first cross-section in an expanded condition and an annulus section with a second cross-section in the expanded condition, the second cross-section being smaller than the first cross-section, the stent including a plurality of struts defining a plurality of cells, and a valve assembly disposed within the annulus section of the stent, the valve assembly including a plurality of leaflets operative to permit blood flow from the annulus section to the aortic section but to substantially block blood flow from the aortic section to the annulus section; and
a graft coupled to the aortic section of the stent, the graft having a body and at least one lining disposed on the body, the body defining a lumen therethrough and including a plurality of legs, each of the legs being formed of a plurality of wire strands, and each of the legs being directly coupled to the aortic section of the stent.

2. The therapeutic device of claim 1, wherein the stent further includes a plurality of retaining elements disposed in the aortic section and the graft is coupled to a strut of the plurality of struts disposed adjacent one of the retaining elements.

3. The therapeutic device of claim 1, wherein the at least one lining is disposed on a luminal surface of the body.

4. The therapeutic device of claim 1, wherein the at least one lining is disposed on an abluminal surface of the body.

5. The therapeutic device of claim 1, wherein the body includes a plurality of braided wire strands.

6. The therapeutic device of claim 5, wherein the plurality of braided wire strands of the body include nitinol.

7. The therapeutic device of claim 1, wherein the graft is collapsible and expandable and configured to fit within an artery.

8. The therapeutic device of claim 1, wherein the body has a generally tubular sidewall with an aperture in the sidewall.

9. The therapeutic device of claim 1, wherein the graft further includes a plurality of radially extending stabilizing wires coupled to the body, the stabilizing wires being grouped to form at least one ring extending around a periphery of the body.

10. The therapeutic device of claim 9, wherein the stabilizing wires are grouped to form multiple rings extending around the periphery of the body, the rings being disposed at different axial positions on the graft.

11. The therapeutic device of claim 1, wherein the body has a plurality of branches, each branch having a lumen in communication with other lumens.

12. The therapeutic device of claim 1, wherein a first portion of the body has a first density, and a second portion of the body has a density different from the first density.

13. The therapeutic device of claim 1, wherein the graft includes multiple linings disposed on the body, the linings being spaced from one another in a length direction of the graft.

14. The therapeutic device of claim 1, further comprising a sealing structure coupled to the graft adjacent the aortic section of the stent.

15. The therapeutic device of claim 14, wherein the sealing structure includes a coil disposed around a periphery of the body.

16. The therapeutic device of claim 1, wherein the body includes a collapsible and expandable metallic ring.

17. The therapeutic device of claim 1, wherein the plurality of wire strands of each of the legs are wrapped around a strut of the plurality of struts of the stent.

18. The therapeutic device of claim 1, wherein the plurality of wire strands of each of the legs are tied to a strut of the plurality of struts of the stent.

19. The therapeutic device of claim 1, wherein the plurality of wire strands of each of the legs are welded to a strut of the plurality of struts of the stent.

20. The therapeutic device of claim 1, wherein the body of the graft is formed from a first material and the at least one lining is formed from a second material different from the first material.

21. A therapeutic device, comprising:
a prosthetic heart valve including a collapsible and expandable stent having an aortic section with a first cross-section in an expanded condition and an annulus section with a second cross-section in the expanded condition, the second cross-section being smaller than the first cross-section, the stent including a plurality of struts defining a plurality of cells, and a valve assembly disposed within the annulus section of the stent, the valve assembly including a plurality of leaflets operative to permit blood flow from the annulus section to the aortic section but to substantially block blood flow from the aortic section to the annulus section; and
a graft coupled to the aortic section of the stent, the graft having a body defining a lumen therethrough and at least one lining disposed on the body, the body being directly coupled to the aortic section of the stent by an arrangement selected from the group consisting of wrapping a portion of the body around one of the plurality of struts, tying a portion of the body to one of the plurality of struts, and welding a portion of the body to one of the plurality of struts,
wherein the portion of the body coupled to the aortic section of the stent includes a plurality of legs, each leg being formed of a plurality of strands.

* * * * *